United States Patent
Tanaka et al.

(10) Patent No.: US 6,205,843 B1
(45) Date of Patent: Mar. 27, 2001

(54) GAS SENSING ELEMENT AND A METHOD FOR MEASURING A SPECIFIC GAS CONCENTRATION

(75) Inventors: Akio Tanaka, Gifu; Tomio Sugiyama, Nagoya; Shinichiro Imamura; Satoshi Hada, both of Kariya; Keigo Mizutani, Okazaki, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/440,859

(22) Filed: Nov. 16, 1999

(30) Foreign Application Priority Data

| Nov. 16, 1998 | (JP) | 10-325047 |
| Jan. 18, 1999 | (JP) | 11-009421 |
| Oct. 6, 1999 | (JP) | 11-285900 |
| Oct. 6, 1999 | (JP) | 11-285901 |

(51) Int. Cl.$^7$ .......................... G01N 27/407; G01N 7/00; G01N 27/46
(52) U.S. Cl. .................. 73/31.06; 73/23.32; 73/31.05; 422/90
(58) Field of Search .................. 73/31.06, 23.32, 73/23.2, 31.05; 422/90, 98

(56) References Cited

U.S. PATENT DOCUMENTS

| 4,051,006 | * | 9/1977 | Neti et al. | 204/195 P |
| 4,627,269 | * | 12/1986 | Forster et al. | 73/233 |
| 4,645,572 | * | 2/1987 | Nishizawa et al. | 204/1 T |
| 5,400,643 | * | 3/1995 | De Angelis et al. | 73/31.06 |
| 5,413,683 | * | 5/1995 | Murase et al. | 204/183.16 |
| 5,493,896 | * | 2/1996 | Reigel | 73/23.31 |
| 5,602,326 | * | 2/1997 | Takahashi et al. | 73/31.06 |
| 5,686,654 | * | 11/1997 | Friese et al. | 73/23.32 |
| 5,763,763 | * | 6/1998 | Kato et al. | 73/23.2 |
| 5,804,699 | * | 9/1998 | Sugiyama et al. | 73/23.32 |
| 5,866,799 | | 2/1999 | Kato et al. | 73/31.05 |
| 5,889,196 | * | 3/1999 | Ueno et al. | 73/23.31 |
| 5,925,814 | * | 7/1999 | Tsuzuki et al. | 73/23.32 |
| 5,948,963 | * | 9/1999 | Kato et al. | 73/23.2 |

FOREIGN PATENT DOCUMENTS

| 0798555 | 10/1997 | (EP) . |
| 64-39545 | 2/1989 | (JP) . |
| 8-271476 | 10/1996 | (JP) . |
| 9-318596 | 12/1997 | (JP) . |

* cited by examiner

Primary Examiner—Hezron Williams
Assistant Examiner—David J. Wiggins
(74) Attorney, Agent, or Firm—Pillsbury Winthrop LLP

(57) ABSTRACT

A gas sensing element having a sample gas chamber into which a sample gas is introduced, and a reference gas chamber into which a reference gas is introduced. A sensor cell detects a specific gas concentration in the sample gas chamber. An oxygen pump cell pump cell pumps oxygen gas from or to the sample gas chamber. An introducing passage includes at least one pinhole provided on a surface of the oxygen pump cell for introducing the measuring gas into the sample gas chamber. The surface of the oxygen pump cell faces an outside of the gas sensing element. And, a porous diffusion resistive layer is provided on the surface of the oxygen pump cell so as to cover a portion corresponding to the introducing passage, thus serving to reduce or eliminate the effects of temperature dependency upon gas sensor output for properly sized and machine pinholes.

13 Claims, 17 Drawing Sheets

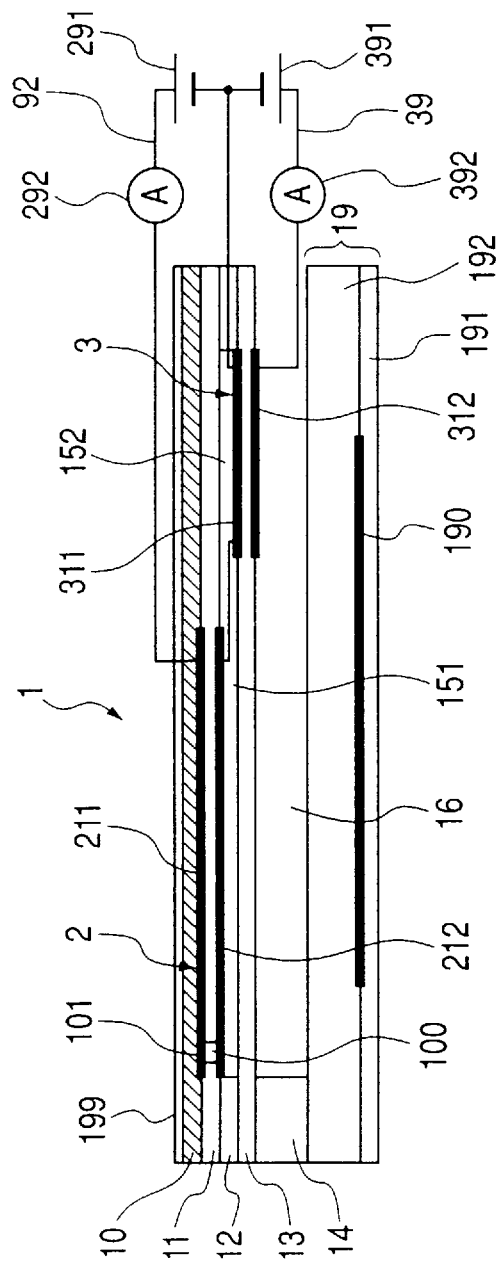
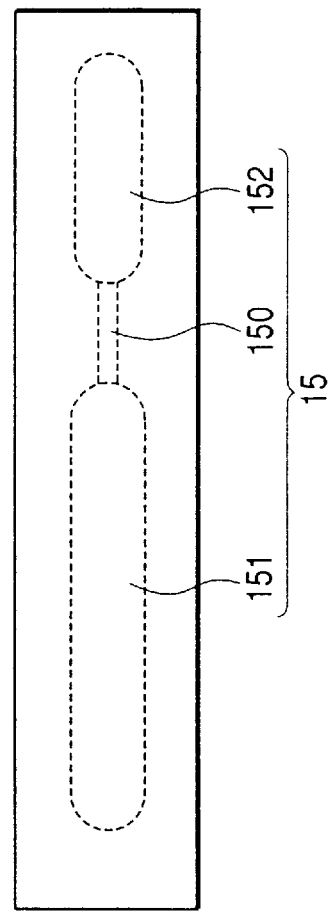

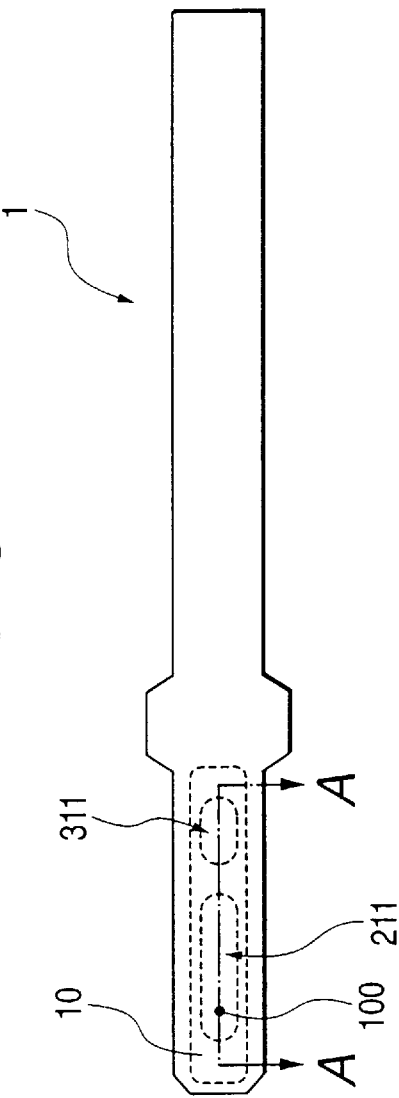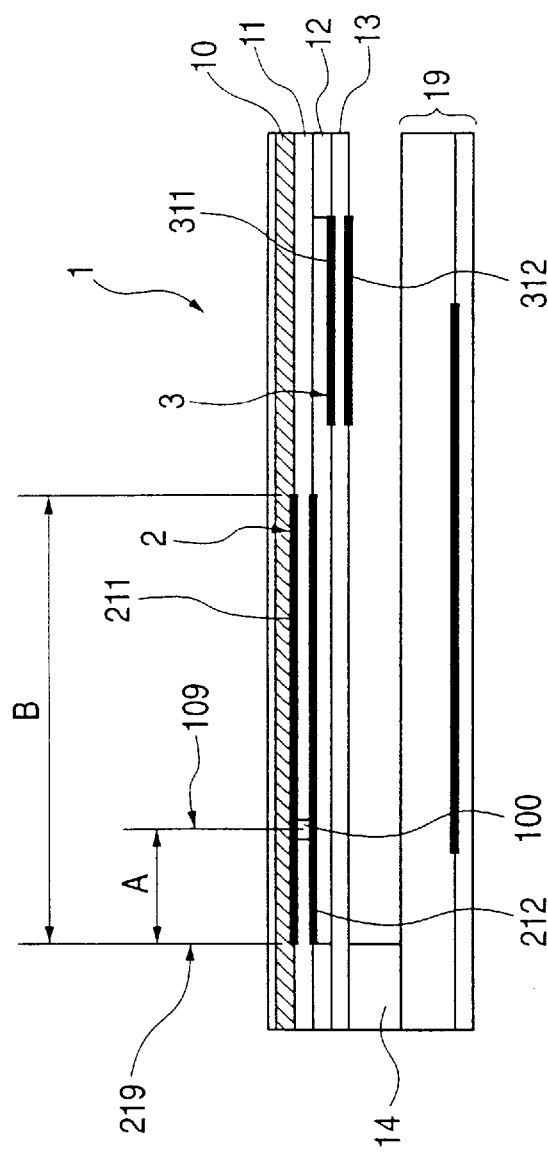

FIG. 5

| SAMPLE No. | INTRODUCING PASSAGE | | POROUS DIFFUSION RESISTIVE LAYER | | | | TEMP. DEPENDENCY | CRACK GENERATION | OUTPUT CURRENT | O2 GAS CONCENTRATION DEPENDENCY | RESPONSE |
|---|---|---|---|---|---|---|---|---|---|---|---|
| | A/B | CROSS SECTION | LOCATION | THICKNESS | POROSITY | MEAN PORE DIAMETER | | | | | |
| 1 | 0 | 0.2mm² | OUTSIDE PUMP ELECTRODE | 100μm | 12% | 1100Å | ○(±5%) | ○(≤1%) | ○(4μA) | ○(±5%) | ○(0.5s) |
| 2 | 0.1 | ← | ← | ← | ← | ← | ← | ← | ○(4μA) | ○(±6%) | ○(0.4s) |
| 3 | 0.5 | ← | ← | ← | ← | ← | ← | ← | ○(4μA) | ○(±7%) | ○(0.3s) |
| 4 | 0.1 | ← | ← | 50μm | ← | ← | ○(±6%) | ← | ○(8μA) | ○(±5%) | ○(0.3s) |
| 5 | ← | ← | ← | 300μm | ← | ← | ○(±4%) | ← | ○(3μA) | ← | ○(0.6s) |
| 6 | ← | ← | NOTHING | 0μm | ← | ← | ×(±10%) | ← | ○(8μA) | ← | ○(0.2s) |
| 7 | ← | ← | SAMPLE GAS CHAMBER | 200μm | ← | ← | ○(±4%) | ×(20%) | ×(0.1μA) | ← | ×(1s) |
| 8 | ← | ← | OUTSIDE PUMP ELECTRODE | 400μm | ← | ← | ○(±4%) | ○(≤1%) | ○(2μA) | ← | ○(0.3s) |
| 9 | 0.6 | ← | ← | 100μm | ← | ← | ○(±5%) | ○(≤1%) | ○(4μA) | ×(±10%) | ○(0.2s) |
| 10 | 0.1 | 0.03mm² | ← | ← | ← | ← | ○(±5%) | ← | ○(1μA) | ○(±5%) | ○(0.3s) |
| 11 | ← | 0.02mm² | ← | ← | ← | ← | ○(±4%) | ← | ×(0.8μA) | ← | ○(0.3s) |
| 12 | ← | 0.7mm² | ← | ← | ← | ← | ○(±4%) | ← | ○(16μA) | ○(±8%) | ○(0.2s) |
| 13 | ← | 0.8mm² | ← | ← | ← | ← | ○(±4%) | ← | ○(20μA) | ×(±10%) | ○(0.2s) |
| 14 | ← | 0.2mm² | ← | ← | 3% | 200Å | ○(±4%) | ← | ○(2μA) | ○(±4%) | ○(0.6s) |
| 15 | ← | ← | ← | ← | 2% | 100Å | ○(±3%) | ← | ×(0.8μA) | ○(±3%) | ×(1s) |
| 16 | ← | ← | ← | ← | 20% | 2000Å | ○(±6%) | ← | ○(5μA) | ○(±8%) | ○(0.2s) |
| 17 | ← | ← | ← | ← | 30% | 3000Å | ○(±8%) | ← | ○(7μA) | ×(±10%) | ○(0.2s) |

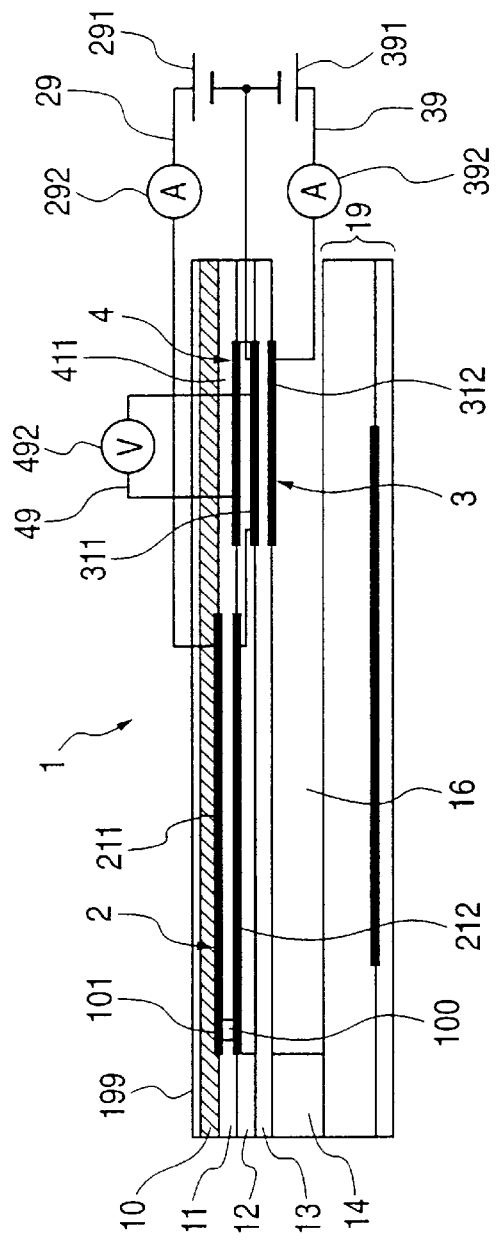
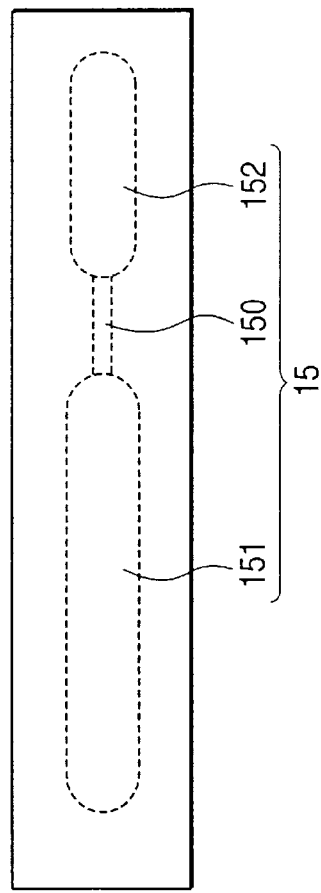

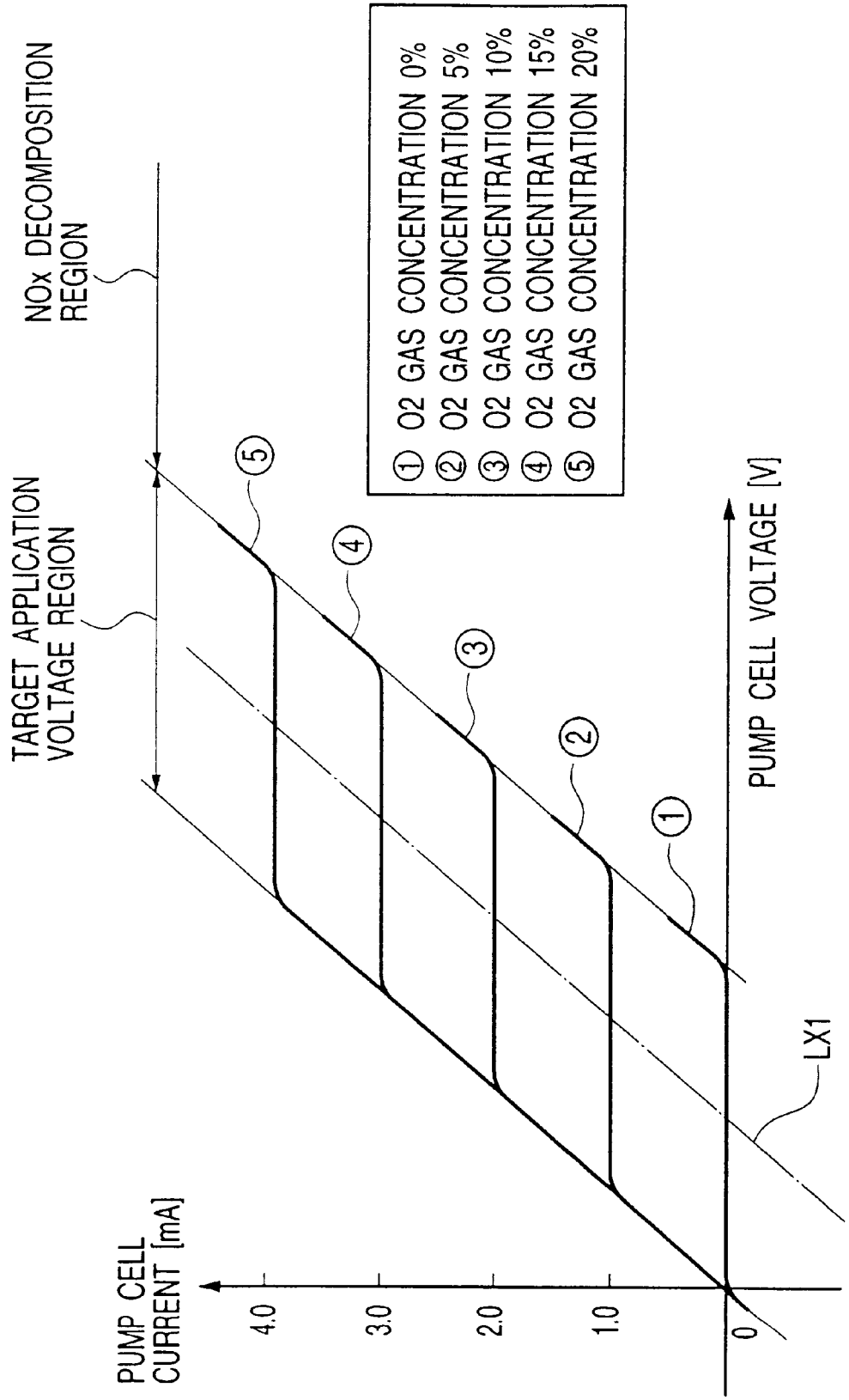

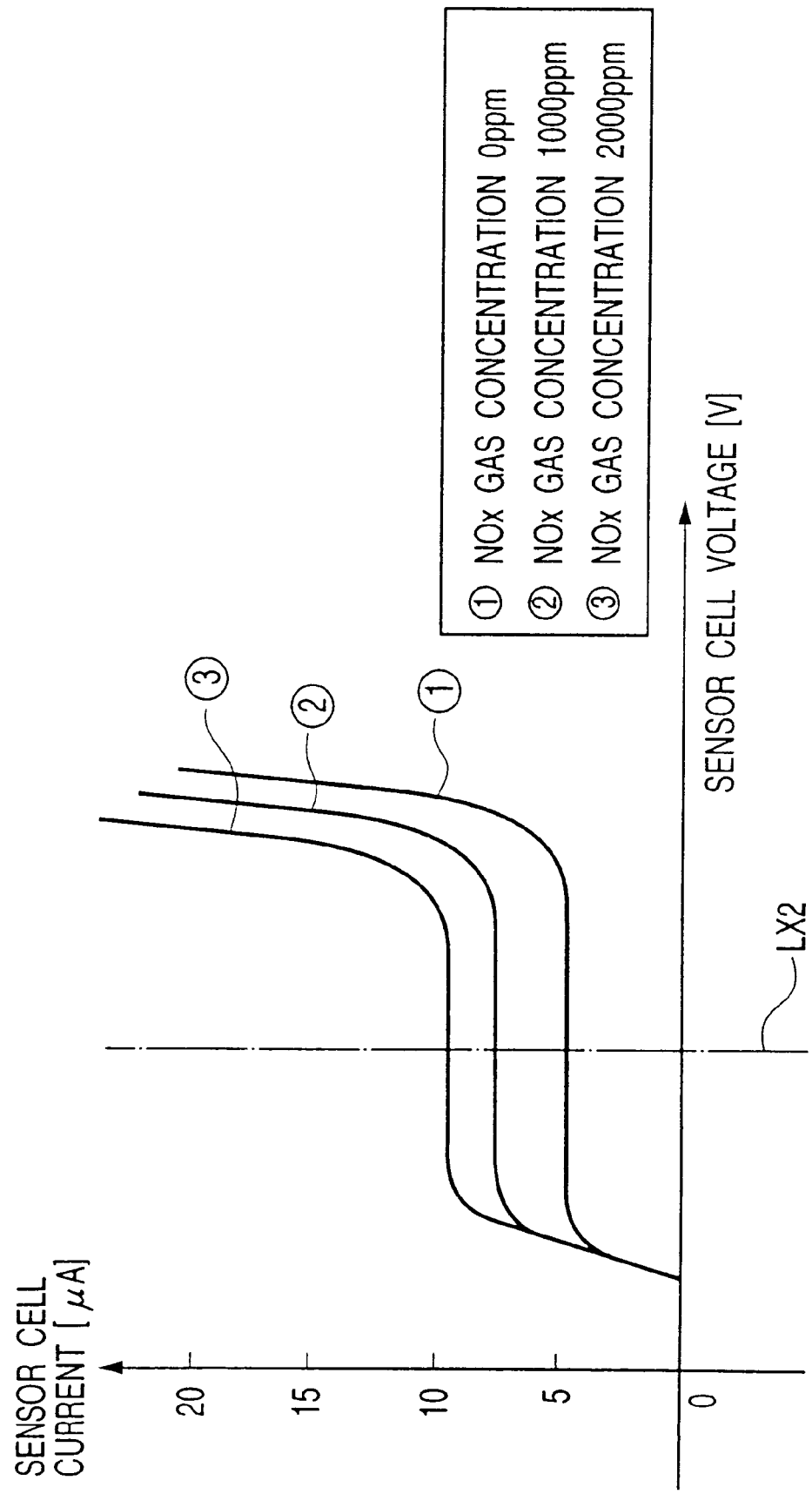

GAS SENSING ELEMENT AND A METHOD FOR MEASURING A SPECIFIC GAS CONCENTRATION

BACKGROUND OF THE INVENTION

The present invention relates to a gas sensing element used in a gas sensor installable in an exhaust gas passage of an internal combustion engine of an automotive vehicle for detecting a specific gas component, such as a NOx gas concentration, contained in the exhaust gas, or an air-fuel ratio sensor incorporated in an air-fuel ratio (A/F) control system of the internal combustion engine, or a sensor for detecting an oxygen gas concentration.

Automotive vehicles exhaust harmful emission gases, such as NOx, HC, CO, that cause serious air pollution. Nowadays, the global warming phenomenon caused by CO2 is a big social problem to be solved.

To prevent air pollution, law regulations have become severe and strict to substantial reduce of harmful emissions exhausted from automotive vehicles and also in detection of deteriorated catalytic converters which may not function to purify the exhaust gases.

To stop the global warming phenomenon, effective countermeasures will include reduction of $CO_2$, restriction in fuel consumption, and favorable treatment in tax.

In the market of automotive vehicles, reduction of harmful emissions and improvement of fuel economy are main goals to be attained to respond to the requirements from the modern society.

To satisfy such requirements, lean burn engines including direct-injection type engines (injecting fuel directly in a combustion chamber) have been developed as prospective engines having the capability of improving the fuel economy of the gasoline engines.

The lean burn techniques are characterized in that the air-fuel ratio (A/F ratio) is set to be a higher level compared with a stoichiometric (or theoretical) value, i.e., 14.7, of the ordinary engines. In general, shifting of the air-fuel ratio to a higher level increases the NOx amount contained in the exhaust gas. The conventional three-way catalytic converters were chiefly developed to purify the stoichiometric exhaust gases. Thus, it is necessary to develop a new exhaust gas purification system effectively applicable to advanced lean burn techniques.

Meanwhile, there are advanced diesel engines that are electronically controlled. Reduction of NOx gas is also important for the diesel engines. In this respect, development of so-called DeNOx catalytic converter systems will be indispensable for the advanced diesel engines.

To develop the NOx catalyst based purification systems, it is important to accurately control the purification rate of the NOx catalyst or monitor the deterioration of the NOx catalyst. To realize this, it is desirable to directly detect the NOx gas concentration of the exhaust gas.

Unexamined Japanese patent publication No. 64-39545 (No. 1-39545) discloses a gas sensing element that is capable of directly detecting the NOx gas concentration of the exhaust gas. This conventional gas sensing element comprises two sets of cells, each consisting of an oxygen pump cell and a sensor cell. Each oxygen pump cell includes electrodes provided on opposite sides of a solid electrolytic member disposed between a sample gas chamber and an exhaust gas passage. Each sensor cell includes electrodes provided on opposite sides of a solid electrolytic member disposed between the sample gas chamber and a reference gas chamber. The exhaust gas is introduced via an introducing port into sample gas chamber. The NOx gas concentration is detectable by measuring an electric current value between the sensor cells.

FIGS. 9A and 9B are views showing another conventional gas sensing element (for example, disclosed in the Unexamined Japanese patent publication No. 8-271476). A gas sensing element 9 comprises two solid electrolytic members 901 and 902 between which a spacer is interposed. A sample gas chamber is formed in this spacer. The sample gas chamber consists of a first chamber 903 and a second chamber 904.

The sample gas is introduced via an introducing passage 905 into the first chamber 903. An oxygen sensor cell 91 detects the oxygen gas concentration in the first chamber 903. A drive voltage of a first oxygen pump cell 92 is feedback controlled so as to equalize a detected oxygen gas concentration with a predetermined value.

The oxygen sensor cell 91 includes two electrodes 911 and 912 provided on a surface of the solid electrolytic member 902. One electrode 911 is exposed to air in an air introducing passage 907, and the other electrode 912 is exposed to the gas in the first chamber 903. The first oxygen pump cell 92 comprises two electrodes 921 and 922 provided on opposite surfaces of the solid electrolytic member 901. One electrode 921 is exposed to the sample gas, and the other electrode 922 is exposed to the gas in the first chamber 903.

The second chamber 904 communicates with the first chamber 903 via a passage 906. A second oxygen pump cell 93 is provided in the second chamber 904 to discharge the oxygen gas from the second chamber 904. The second oxygen pump cell 93 comprises two electrodes 911 and 932 provided on the surface of the solid electrolytic member 902. The electrode 932, having NOx deoxidizing properties, is exposed to the gas in the second chamber 904.

In the second chamber 904, NOx contained in the exhaust gas is deoxidized and decomposed so as to newly generate oxygen gas. The pump current flowing through the second oxygen pump cell 93 increases or decreases in response to the generated oxygen gas.

The oxygen gas, contained in the sample gas diffusing from the first chamber 903 to the second chamber 904, has a constant concentration. From this fact, it is believed that the increase or decrease of the pump current is dependent on the deoxidization of NOx. In other words, the NOx gas concentration is detectable by measuring the pump current.

However, the introducing passage of the above-described gas sensing element is a pinhole which is usually formed by machining. The pinhole is formed by opening a through hole extending vertically across a sheet serving as a solid electrolytic member.

The gas amount diffusing through the pinhole is dependent on the ambient temperature T. Usually, when the pinhole is formed by machining, the gas diffusion amount is proportional to $T^{1.75}$.

For this reason, the output current of the sensor element has temperature dependency. When the exhaust gas temperature changes in a wide range, a significant measuring error will be caused.

This is a common problem raised in gas sensor elements which are used for detecting the concentration of specific gas components, such as $O_2$, HC and CO, involved in the sample gas.

SUMMARY OF THE INVENTION

In view of the foregoing problems encountered in the prior art, the present invention has an object to provide a gas sensing element which is capable of eliminating measuring errors in severe circumstances where the temperature of the sample gas changes in a wide range.

Another object of the present invention is to provide a method for measuring a specific gas concentration as well as an oxygen gas concentration of a sample gas with a sensing element having a simplified structure.

In order to accomplish this and other related objects, the present invention provides a gas sensing element comprising a sample gas chamber into which a sample gas is introduced, a reference gas chamber into which a reference gas is introduced, a sensor cell located in both of the sample gas chamber and the reference gas chamber for detecting the concentration of a specific gas contained in the sample gas, an oxygen pump cell located in the sample gas chamber for pumping oxygen gas from or to the sample gas chamber, and an introducing passage including at least one pinhole provided on an outer surface of the oxygen pump cell for introducing the sample gas into the sample gas chamber. The outer surface of the oxygen pump cell faces an outside of the gas sensing element. And, a porous diffusion resistive layer is provided on the outer surface of the oxygen pump cell so as to cover a portion corresponding to the introducing passage.

The gas sensing element of the present invention is characterized in that the introducing passage, constituted by the pinhole, is provided on the surface of the oxygen pump cell and the inlet of the introducing passage is covered by the porous diffusion resistive layer. The surface of the oxygen pump cell directly or indirectly faces the outside of the gas sensing element. The sample gas, e.g., exhaust gas, is introduced from the outside space into the sample gas chamber in the gas sensing element via the introducing passage.

The introducing passage may be a pinhole (through hole) having a circular or polygonal cross section. It is possible to provide a plurality of introducing passages.

The porous diffusion resistive layer may be provided in a limited surface region of a solid electrolytic member. In this case, the limited surface region includes the surface of the oxygen pump cell. Alternatively, it is possible to cover the entire surface of the solid electrolytic member by the porous diffusion resistive layer.

It is preferable to provide a trap layer covering the surface of the porous diffusion resistive layer. The trap layer functions as a means for trapping poisonous substances in the sample gas, thereby preventing the poisonous substances from reaching the porous diffusion resistive layer. Furthermore, when the gas sensing element of the present invention is used to measure the specific gas component involved in the exhaust gas emitted from engines, it is possible to provide a catalytic layer to equilibrate the unburned gases in the exhaust gas.

According to preferred embodiments, the oxygen pump cell includes an inside pump electrode and an outside pump electrode provided on opposite surface a of the solid electrolytic member. In this case, the inside pump electrode faces the sample gas chamber, and the outside pump electrode faces the outside of the gas sensing element. The introducing passage is provided on the outside pump electrode.

The gas sensing element of the present invention functions in the following manner:

First, the sample gas penetrates or passes through the porous diffusion resistive layer before the sample gas reaches the inlet of the introducing passage. And then, the sample gas is introduced into the sample gas chamber via the introducing passage.

The diffusing of the sample gas in the porous diffusion resistive layer include both the Knudsen diffusion and the molecular diffusion. Thus, the caused diffusion is less dependent on the temperature. The diffusion amount of the sample gas introduced into the sample gas chamber is substantially constant irrespective of high or low (or increase or decrease) of the temperature.

The oxygen pump cell of the present invention functions as a means for pumping the oxygen gas from the sample gas chamber to adjust the oxygen gas concentration in the sample gas chamber to a constant value or to discharge the oxygen gas from the sample gas chamber.

The sensor cell is capable of deoxidizing a specific gas (e.g., NOx gas) component in the sample gas chamber. Oxygen ions are separated from the specific gas due to this deoxidization function. The generated oxygen ions cause an ion current. By measuring this ion current, it becomes possible to obtain an output current which is responsive to the specific gas amount in the sample gas chamber.

According to the gas sensing element of the present invention, the diffusion amount of the sample gas is less dependent on the temperature. Thus, a constant amount of sample gas is introduced into the sample gas chamber irrespective of high and low of the temperature. A measured specific gas concentration of the sample gas chamber is proportional to the actual specific gas concentration of the measuring gas irrespective of high and low of the present invention. Thus, the present invention provides a gas sensing element having small or negligible temperature dependency in the measuring accuracy. Therefore, the gas sensing element of the present invention can be preferably used in severe circumstances in which the measuring gas temperature varies widely.

Furthermore, the introducing passage is provided in the region corresponding to the oxygen pump cell. It is advantageous in that the oxygen pump cell can effectively pump (discharge or introduce) the oxygen gas from or to the sample gas chamber immediately after the sample gas is introduced into the sample gas chamber. Thus, it becomes possible to surely pump the oxygen gas from the sample gas in advance before the sample gas reaches the sensor cell. Hence, the adverse influence of oxygen gas concentration can be surely removed in the output current of the gas sensing element.

It is preferable that the oxygen pump cell comprises an outside pump electrode provided on the outer surface thereof, and a relationship $A/B \leq 0.5$ is established when "A" represents a distance from a central position of the introducing passage to a front edge of the outside pump electrode and "B" represents the length of the outside pump electrode. With this arrangement, the oxygen pump cell can possess an enhanced and sufficient oxygen gas discharge function. In other words, an offset current (i.e., a current obtained when no specific gas is contained in the sample gas) can be stabilized.

When the ratio A/B is larger than 0.5, the oxygen gas in the sample gas chamber may not be discharged sufficiently the oxygen pump cell. When the sample gas containing excessive or residual oxygen gas reaches the sensor cell, a measured sensor current will include an error component corresponding to the excessive or residual oxygen gas. In other words, the offset current deviates from a true value. Thus, the sensor output may have oxygen gas concentration dependency.

The minimum value of the ratio A/B is 0. When the ratio A/B is 0, the introducing passage is located at the front end of the outside pump electrode. In this case, the sensor cell is far from the introducing passage and is positioned at the same side as the other (i.e., rear) end of the outside pump electrode.

The central position of the introducing passage is a geometrical center or a centroid of a cross section of the introducing passage. When a plurality of introducing passages are provided, the distance "A" is defined based on the central position of the farthest introducing passage from the front end of the pump electrode.

The length of the outside pump electrode is a distance from the front end thereof to the rear end thereof.

Preferably, the introducing passage has a total cross-sectional area in a range from 0.02 to 0.8 $mm^2$.

When the total cross-sectional area is not larger than 0.02 $mm^2$, the introducing passage is too small to accurately open the pinhole in the manufacturing process of the gas sensing element. Furthermore, an obtainable output current of the sensor is too small to avoid adverse influence of noise or the like.

When the total cross-sectional area is not smaller than 0.8 $mm^2$, an excessive amount of sample gas is introduced into the sample gas chamber at a time via the introducing passage. In such a case, the oxygen pump cell cannot pump the oxygen gas sufficiently. The output current obtained from the sensor cell cannot accurately represent the specific gas concentration.

Preferably, the introducing passage is formed by machining.

The manufacturing of the gas sensing element is simplified. The sensor current value is stabilized.

Preferably, the porous diffusion resistive layer has a thickness in a range from 0.05 to 0.3 mm.

This effectively prevents the porous diffusion resistive layer from being cracked during the sintering process of the gas sensing element. The sensor properties can be stabilized.

When the thickness of the porous diffusion resistive layer is less than 0.05 mm, the temperature dependency of the gas sensing element is worsened. When the thickness of the porous diffusion resistive layer exceeds 0.3 mm, the sensor response is worsened.

Preferably, the porous diffusion resistive layer has a mean pore diameter in a range from 200 to 2,000 Å. The sensor properties can be stabilized.

When the mean pore diameter is less than 200 Å, the sample gas cannot smoothly diffuse in the porous diffusion resistive layer. The sensor response is worsened, and the output current becomes small. When the mean pore diameter is larger than 2,000 Å, the diffusion of the sample gas becomes unstable. The sensor output may have oxygen gas concentration dependency.

Preferably, the porous diffusion resistive layer has a porosity in a range from 3 to 20%. The sensor properties can be stabilized.

When the porosity is less than 3%, the sample gas cannot smoothly diffuse in the porous diffusion resistive layer. The sensor response is worsened, and the output current becomes small. When the porosity is larger than 20%, the sensor output may have oxygen gas concentration dependency.

Preferably, the sample gas chamber faces both of a first solid electrolytic member and a second solid electrolytic member. The reference gas chamber faces the second solid electrolytic member. And, the oxygen pump cell is provided on the first solid electrolytic member and the sensor cell is provided on the second solid electrolytic member.

This arrangement is effective to eliminate the current interference caused between the oxygen pump cell and the sensor cell. It becomes possible to accurately measure the gas concentration.

Preferably, a relationship $0.5 \leq D2/(D1+D2) \leq 0.9$ is established when D1 represents a diffusion resistance of the introducing passage and D2 represents a diffusion resistance of the porous diffused layer. The sensor output can be stabilized.

When the ratio $D2/(D1+D2)$ is less than 0.5, the diffusion resistance of the introducing passage (i.e., molecular diffusion) becomes too large to suppress or eliminate the temperature dependency in the sensor output.

When the ratio $D2/(D1+D2)$ is larger than 0.9, the diffusion resistance of the porous diffused layer becomes too large to obtain appropriate sensor response.

When other diffusion resistances in an inside space is negligibly small compared with the above-described two representative diffusion resistances, D1 and D2 can be expressed in the following manner.

$$Is = (D1+D2) ln\{P/((1-P_{NOx})\}$$

where Is represents an sensor output, $P_{NOx}$ represents a partial pressure of NOx, and P represents a total pressure.

D1 and D2 are dependent on the geometrical configuration and are indirectly measurable from a sensor current difference between a sensor element having no porous diffusion resistive layer and a sensor element having a porous diffusion resistive layer.

Another aspect of the present invention provides a method for measuring a specific gas concentration of a sample gas by using a simple gas sensing element. The gas sensing element comprises a sensor cell including a measuring electrode and a reference electrode provided on a solid electrolytic member, the measuring electrode being located in a sample gas chamber and the reference electrode being located in a reference gas chamber, a pump cell including a pair of pump electrodes provided on opposite surfaces of another solid electrolytic member, one of the pump electrodes being located in the sample gas chamber, a sensor circuit including a first ammeter and a power supplier for measuring a current flowing in the sensor cell, and a pump circuit including a second ammeter and a variable power supplier for measuring a current flowing in the pump cell. The method of the present invention comprises a first step of measuring an oxygen gas concentration of a sample gas based on a current value measured by the second ammeter, a second step of controlling the variable power supplier based on a measured oxygen gas concentration value, and a third step of measuring a specific gas concentration of the sample gas based on a current value measured by the first ammeter.

According to the measuring method of the present invention, the pump circuit includes the variable power supplier for applying the voltage to the pump cell. The pump circuit includes the second ammeter. In response to the voltage applied to the pump cell, the oxygen gas in the sample gas chamber ionizes on the surface of the pump electrode. Oxygen ions are discharged out of the sample gas chamber via the solid electrolytic member.

The pump cell current increases in proportion to the applied voltage when the application voltage value is small, as later described with reference to FIG. 16. When the applied voltage reaches a predetermined level, the pump cell current stops increasing irrespective of change of the applied voltage. This region is referred to as a limit-current region. When the applied voltage increases to a further higher level, the pump cell current restarts increasing in proportion to the applied voltage. In general, the voltage-current characteristic curve shifts along an oblique line ascending in the right direction in response to the oxygen gas concentration.

Accordingly, an adjusted voltage is applied to the pump cell from the variable power supplier based on a measured current of the second ammeter so that the limit current flows through the pump cell. The oxygen gas is discharged out of the sample gas chamber so as to adjust the air-fuel ratio in the sample gas chamber to a theoretical (i.e., stoichiometric) value. Accordingly, the oxygen amount in the sample gas chamber is maintained at a constant value of approximately $1 \times 10^{-6}$ atm.

As the limit-current value is proportional to the oxygen gas concentration, the pump circuit can be used to measure the oxygen gas concentration of the sample gas introduced into the sample gas chamber.

The power supplier in the sensor circuit applies the voltage to the sensor cell. The sensor circuit includes the first ammeter.

The specific gas (e.g., NOx gas) contained in the sample gas is deoxidized on the measuring electrode in response to the voltage applied to the sensor cell. As the voltage is applied between the measuring electrode and the reference electrode, the produced oxygen ions cause an ion current flowing across the solid electrolytic member of the sensor cell as a current representing the specific gas component contained in the sample gas.

The ion current flows in the sensor circuit connected to the sensor cell. The first ammeter measures the ion current. The ion current varies in accordance with the specific gas concentration. Thus, it is possible to measure the specific gas concentration based on a measured current value of the first ammeter.

Furthermore, almost all of the oxygen gas residing in the sample gas chamber is discharged in advance by the pump electrode. It is therefore believed that all of the oxygen ions ionized on the sensor cell derive from the deoxidization of the specific gas. Thus, it is possible to measure the specific gas concentration based on the measured current value of the first ammeter.

In this manner, the present invention provides the method for measuring both the specific gas concentration and the oxygen gas concentration by using only the pump cell and the sensor cell. Thus, the present invention provides a gas concentration measuring method realized by a simplified sensing element structure. The gas sensing element can be simply manufactured. As the required number of electrodes is small, it becomes possible to reduce the total amount of expensive noble or precious metals. Thus, the manufacturing cost can be reduced.

According to the present invention, the gas concentration element can be used to measure the concentration of various specific gases by changing the type (or properties) of a measuring electrode of the sensor cell.

For example, the gas sensing element of the present invention functions as a NOx gas sensing element by using a measuring electrode having the chemical activity against NOx gas. More specifically, it is preferable that the measuring electrode is constituted by a material capable of decomposing NOx gas into nitrogen ions and oxygen ions.

The decomposed oxygen ions flow across the solid electrolytic member to cause an ion current. By measuring this ion current, it becomes possible to obtain the data representing the NOx gas concentration. In this manner, the gas sensing element of the present invention can operate as a NOx gas sensing element.

Besides NOx gas, the gas sensing element of the present invention can be used to measure the concentration of other specific components, such as CO, HC, and $H_2O$, contained in the exhaust gas emitted from the internal combustion engines.

According to the gas sensing element of the present invention, the pump electrodes are exposed to the sample gas. It is therefore necessary to use the pump electrodes having no chemical activity against the sample gas.

As described above, the gas sensing element of the present invention measures the specific gas concentration based on the amount of oxygen ions produced by the decomposition of the specific gas. Accordingly, to ensure the accuracy in the measurement of the specific gas concentration, it is necessary to prevent the pump cell from consuming the specific gas before the specific gas reaches the sensor cell.

It is possible to locate the pump cell so as to face the sample gas chamber and also to face the outside of the gas sensing element. Alternatively, it is possible to locate the pump cell so as to face both the sample gas chamber and the reference gas chamber.

According to a preferred embodiment, the gas sensing element has only one sample gas chamber filled with a porous member. The porous member has a porosity in a range from 3 to 30%. Filling the sample gas chamber by the porous member is effective to maintain the configuration of the sample gas chamber during the manufacturing process or in use of the gas sensing element. The gas sensing element is thus free from deformation or size error. In each sensing element, the characteristics deviation is minimized. The manufacturing cost is reduced. And, the manufacturing process is simplified. As the sample gas chamber has a firm configuration, the present invention makes it possible to provide a gas sensing element having higher measuring accuracy.

The sample gas diffuses in the porous member filling the sample gas chamber. In this case, the diffusion of the sample gas includes both the Knudsen diffusion and the molecular diffusion. Thus, temperature dependency of the sensor output is suppressed within an appropriate level. Accordingly, the present invention provides a gas sensing element having excellent measuring accuracy.

BRIEF DESCRIPTION OF THE DRAWINGS

The above and other objects, features and advantages of the present invention will become more apparent from the following detailed description which is to be read in conjunction with the accompanying drawings, in which:

FIG. 1A is a cross-sectional view showing a detailed arrangement of a gas sensing element in accordance with a first embodiment of the present invention, taken along a line A—A shown in FIG. 2;

FIG. 1B is a plane view showing an arrangement of a sample gas chamber of the gas sensing element shown in FIG. 1A;

FIG. 2 is a plane view showing the gas sensing element in accordance with the first embodiment of the present invention;

FIG. 3 is a cross-sectional view illustrating a relationship between a distance "A" and a length "B" in the gas sensing element in accordance with the first embodiment of the present invention, wherein "A" represents the distance from a central position of an introducing passage to a front edge of an outside pump electrode, and "B" represents the length of the outside pump electrode;

FIG. 5 is a table showing evaluated performances of the gas sensing element in accordance with the first embodiment of the present invention;

FIG. 8A is a cross-sectional view showing a detailed arrangement of a gas sensing element in accordance with a second embodiment of the present invention, in which an oxygen sensor cell is provided;

FIG. 8B is a plane view showing an arrangement of the sample gas chamber of the gas sensing element shown in FIG. 8A;

FIG. 16 is a graph showing a plurality of voltage-current characteristic curves of a pump cell corresponding to various oxygen gas concentration values;

FIG. 17 is a graph showing a plurality of voltage-current characteristic curves of a sensor cell corresponding to various NOx gas concentration values;

DESCRIPTION OF THE PREFERRED EMBODIMENTS

Figure 4A:
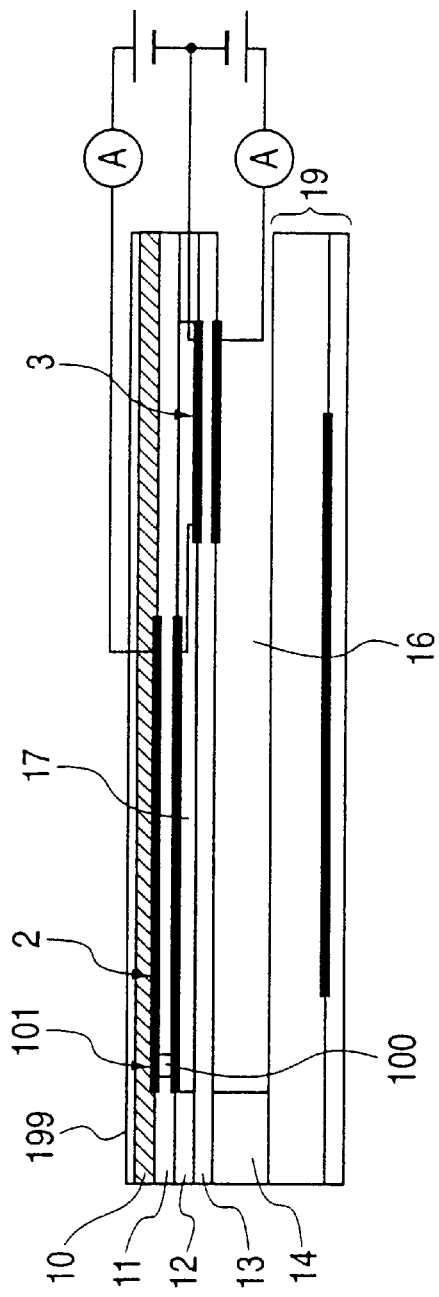
FIG. 4A is a cross-sectional view showing a detailed arrangement of another gas sensing element in accordance with the first embodiment of the present invention, in which only one sample gas chamber is provided.

Preferred embodiments of the present invention will be explained hereinafter with reference to attached drawings.

First Embodiment

FIGS. 1A to 4B show a gas sensing element in accordance with a first embodiment of the present invention, which is preferably installed in an exhaust system of an internal combustion engine to measure a NOx gas concentration of the exhaust gas.

As shown in FIGS. 1A and 1B, the gas sensing element 1 of the first embodiment comprises a sample gas chamber 15, a sensor cell 3, an oxygen pump cell 2, and an introducing passage 100. The sample gas, e.g., exhaust gas, is introduced into the sample gas chamber 15. The sensor cell 3 faces a second chamber 152 of the sample gas chamber 15 at one side (i.e., at the upper side in FIG. 1A) and also faces a reference gas chamber 16 at an opposite side (i.e., at the lower side in FIG. 1A). Air, serving as a reference gas, is introduced into the reference gas chamber 16. The sensor cell 3 detects the NOx gas concentration in the sample gas chamber 15. The oxygen pump cell 2, located at a position longitudinally offset from the sensor cell 3, faces a first chamber 151 of the sample gas chamber 15. The oxygen pump cell 2 pumps (discharges or introduces) the oxygen gas from or to the sample gas chamber 15. The introducing passage 100, extending vertically across the oxygen pump cell 2, introduces the sample gas into the sample gas chamber 15.

The outer (i.e., upper) surface of the oxygen pump cell 2 faces the outside of the gas sensing element 1. A porous diffusion resistive layer 10 is provided on the outer (i.e., upper) surface of the oxygen pump cell 2 so that a portion corresponding to the introducing passage 100 is covered by the porous diffusion resistive layer 10. The porous diffusion resistive layer 10, which is made of an alumina ceramic, is 0.1 mm in thickness, 1,100 Å in a mean pore diameter, and 12% in porosity. As shown in FIG. 2, only one introducing passage 100 is provided. The introducing passage 100 has a cross-sectional area of 0.125 mm$^2$. And, a relationship D2/(D1+D2)=0.7 is satisfied when D1 represents a diffusion resistance of the introducing passage 100 and D2 represents a diffusion resistance of the porous diffusion resistive layer 10.

More specifically, as shown in FIG. 1A, the gas sensing element 1 comprises a first solid electrolytic member 11, a first spacer 12 for defining the sample gas chamber 15, a second solid electrolytic member 13, a second spacer 14 for defining the reference gas chamber 16, and a heater 19. These plane members 11 to 14 and 19 are laminated or stacked so as to constitute a multilayered sensing element body.

Each of the first and second solid electrolytic members 11, 13 is made of a partially stabilized zirconia having the oxygen ion conductivity. Each of the first and second spacers 12 and 14 is made of an alumina ceramic having the insulating properties. The gas sensing element of the first embodiment has two cells, i.e., the oxygen pump cell 2 and the sensor cell 3.

The oxygen pump cell 2 comprises an inside pump electrode 212 and an outside pump electrode 211 provided on opposite surfaces (i.e., lower and upper surfaces) of the first solid electrolytic member 11. The inside pump electrode 212 faces the first chamber 151 of the sample gas chamber 15. The outside pump electrode 211 faces the outside of the gas sensing element 1.

A pinhole, serving as the introducing passage 100, is provided as a through hole extending vertically across the laminated layers of the pump electrodes 211, 212 and the first solid electrolytic member 11. An inlet 101 of the introducing passage 100 is positioned on the surface of the outside pump electrode 211.

As shown in FIG. 2, the porous diffusion resistive layer 10 covers a surface area including the inlet 101 of the introducing passage 100, the outside pump electrode 211, and part of the first solid electrolytic member 11. The outside surface of the porous diffusion resistive layer 10 is covered by a trap layer 199. The trap layer 199 protects the porous diffusion resistive layer 10 against poisonous substances contained in the sample gas.

The inside pump electrode 212 is a Pt—Au electrode. The outside pump electrode 211 is a Pt electrode.

As shown in FIG. 1B, the sample gas chamber 15 consists of the first chamber 151 in which the oxygen pump cell 2 is located and the second chamber 152 in which the sensor cell 3 is located. The first chamber 151 communicates with the second chamber 152 via a diffusion passage 150, so as to allow the sample gas to flow in a direction from the first chamber 151 to the second chamber 152 or in the opposite direction.

As shown in FIG. 1A, the sensor cell 3 comprises a measuring electrode 311 and a reference electrode 312 provided on opposite surfaces (i.e., upper and lower surfaces) of the second solid electrolytic member 13. The measuring electrode 311 faces the second chamber 152 of the sample gas chamber 15. The reference electrode 312 faces the reference gas chamber 16 which is defined by the second spacer 14 located adjacent to the second solid electrolytic member 13. Both of the measuring electrode 311 and the reference electrode 312 are Pt electrodes.

The heater 19 is located next (downside) to the second spacer 14 defining the reference gas chamber 16. The heater 19 comprises a heater substrate 191, a heating section 190, leads, and a shielding substrate 192 covering these members. Each of the heater substrate 191 and the shielding substrate 192 is made of an alumina.

As shown in FIG. 3, according to the gas sensing element 1 of the first embodiment, a distance "A" is 1 mm and a length "B" is 10 mm. Thus, a ratio A/B is 0.1. In this case, "A" represents a distance from a central position 109 of the introducing passage 100 to a front edge 219 of the outside pump electrode 211, and "B" represents the length of the outside pump electrode 211.

Although not shown in FIG. 1A, leads and terminals of the outside pump electrode 211 and the inside pump electrode 212 are provided on the first solid electrolytic member 11. An oxygen pump cell circuit 29 is provided to supply electric power to the oxygen pump cell 2 via the leads and terminals. The oxygen pump cell circuit 29 comprises a power supplier 291 for applying a voltage to the oxygen pump cell 2 and an ammeter 292 for measuring a current in the oxygen pump cell circuit 29.

Similarly, leads and terminals of the measuring electrode 311 and the reference electrode 312 are provided on the second solid electrolytic member 13. A sensing circuit 39 is connected to the leads and terminals of the measuring electrode 311 and the reference electrode 312. The sensing circuit 39 comprises a power supplier 391 for applying a voltage to the sensor cell 3 and an ammeter 392 for measuring a current in the sensing circuit 39.

The gas sensing element 1 is manufactured in the following manner.

Each of the first solid electrolytic member 11 and the second solid electrolytic member 13 is a $ZrO_2$ sheet.

First, a powder of 94 wt % $ZrO_2$ is mixed with a powder of 6 wt % $Y_2O_3$ to obtain a $Y_2O_3$ partially stabilized $ZrO_2$ having a mean grain size of 0.5 µm. Then, the resultant $Y_2O_3$ partially stabilized $ZrO_2$ (100 weight part) is mixed with the materials of $\alpha$-$Al_2O_3$ (1 weight part), PVB (5 weight part), DBP (10 weight part), ethanol (10 weight part) and toluene (10 weight part) to obtain a ceramic mixture. PVB is polyvinyl butyral, and DBP is dibutyl phthalate.

Then, a slurry of the prepared ceramic mixture is formed in a ball mill. The resultant slurry is dried by using the doctor blade method to obtain a green zirconic sheet having a thickness of 0.2 mm in a dried condition.

The green sheet of the first solid electrolytic member 11 is manufactured in the following manner.

The green zirconic sheet is cut into a rectangular shape of 5 mm×80 mm. A vertical through hole is opened across the zirconic sheet to electrically connect the associated electrode to the terminal via the lead.

Next, a Pt paste containing 1–10 wt % Au is applied on the surface of the green zirconic sheet by the screen printing method to form a print pattern of the inside pump electrode 212. Similarly, the print pattern of the outside pump electrode 211, as well as print patters of the associated leads and terminals, are formed by using a Pt paste.

Thereafter, a pinhole having a diameter of 0.5 mm (equivalent to 0.2 $mm^2$ in cross-sectional area), serving as the introducing passage 100, is opened by using a punching machine or the like. The position of this pinhole is in the region corresponding to the print pattern of the outside pump electrode 211.

When the green sheet is sintered, it shrinks 20% in the dimensions. Thus, the introducing passage 100 becomes 0.4 mm in diameter (=0.125 $mm^2$ in the cross-sectional area) in the dried (i.e., sintered) condition of the sheet.

The green sheet of the second solid electrolytic member 13 is manufactured in the following manner.

The green zirconic sheet is cut into a rectangular shape of 5 mm×80 mm. A vertical through hole is opened across the zirconic sheet to electrically connect the associated electrode to the terminal via the lead.

Next, the print patterns of the measuring electrode 311 and the reference electrode 312, as well as print patters of the associated leads and terminals, are formed by using a Pt paste.

A green sheet for the first spacer 12, the second spacer 14, the heater substrate 191, and the shielding substrate 192 is manufactured in the following manner.

A powder of $\alpha$-$Al_2O_3$ having a mean grain size of 0.3 µm (98 weight part) is mixed with the above-described $Y_2O_3$ partially stabilized $ZrO_2$ (3 weight part), PVB (10 weight part), DBP (10 weight part), ethanol (30 weight part) and toluene (30 weight part) to obtain a ceramic mixture. As described above, the $Y_2O_3$ partially stabilized $ZrO_2$ is a mixture of a powder of 94 wt % $ZrO_2$ and a powder of 6 wt %$Y_2O_3$.

Then, a slurry of the prepared ceramic mixture is formed in the ball mill. The resultant slurry is dried by using the doctor blade method to obtain a green alumina sheet having a thickness of 0.2 to 1.0 mm in a dried condition.

The obtained green alumina sheet is cut into a U-shape configuration of 5 mm×80 mm with a cutout (window) of 2 mm×75 mm. The resultant sheet serves as the second spacer 14 for defining the reference gas chamber. Another green aluminum sheet is cut into a rectangular shape of 5 mm×80 mm with two elliptic bores connected via a thin passage as shown in FIG. 1B. The resultant sheet serves as the first spacer 12.

Another green alumina sheet is cut into a rectangular shape of 5 mm×80 mm. An electrically-conductive paste, containing 90 wt % Pt and 10 wt % $Al_2O_3$, is applied on the surface of this alumina sheet to form print patterns of the heating section 190 and associated leads. The resultant sheet serves as the heater substrate 191.

Another green alumina sheet is cut into a rectangular shape of 5 mm×80 mm. The resultant sheet serves as the shielding substrate 192.

A green sheet for the porous diffusion resistive layer 10 is manufactured in the following manner.

A powder of α-$Al_2O_3$ having a mean grain size of 0.5 μm (98 weight part) is mixed with the above-described $Y_2O_3$ partially stabilized $ZrO_2$ (3 weight part), PVB (10 weight part), DBP (10 weight part), ethanol (30 weight part) and toluene (30 weight part) to obtain a ceramic mixture. As described above, the $Y_2O_3$ partially stabilized $ZrO_2$ is a mixture of a powder of 94 wt % $ZrO_2$ and a powder of 6 wt %$Y_2O_3$.

Then, a slurry of the prepared ceramic mixture is formed in the ball mill. The resultant slurry is dried by using the doctor blade method to obtain a green alumina sheet having a thickness of 0.12 mm in a dried condition.

The obtained green alumina sheet is cut into a rectangular shape of 5 mm×30 mm. The resultant sheet serves as the porous diffusion resistive layer 10.

The above-described sheets are laminated or put one on another in a manner shown in FIG. 1A and are united by a pressure-sensitive adhesive paste at a room temperature. Then, the resultant laminated body is sintered in the air at about 1,500° C. for one hour to obtain the multilayered gas sensing element 1.

After then, dipping of a slurry of $Al_2O_3$ (50 weight part), inorganic binder (10 weight part), and water (40 weight part) is applied on the sintered porous diffusion resistive layer 10. The applied slurry is dried and baked at the temperature of 500° C. for one hour, thereby forming the trap layer 199.

The gas sensing element of the above-described first embodiment detects the NOx gas concentration of the sample gas in the following manner.

The sample gas penetrates the trap layer 199 and the porous diffusion resistive layer 10. Then, the sample gas is introduced into the first chamber 151 of the sample gas chamber 15 from the inlet 101 via the introducing passage 100.

The voltage of the power supplier 291 is applied between the outside pump electrode 211 and the inside power electrode 212 of the oxygen pump cell 2. The inside pump electrode 212 is a Pt—Au electrode that is inactive against NOx gas. Accordingly, the oxygen pump cell 2 pumps an oxygen gas by an amount corresponding to the applied voltage and discharges the pumped oxygen gas out of the gas sensing element 1.

In this case, the voltage applied from the power supplier 291 is adjusted to a predetermined value so that no decomposition of the NOx gas occurs and the oxygen gas can be smoothly discharged from the sample gas chamber 15.

To perform this adjustment, an actual current value flowing through the oxygen pump cell 2 is measured beforehand by applying a specific voltage. Based on the current value detectable by a control circuit or the like, an optimum voltage applied from the power supplier 291 is calculated in advance.

The sample gas containing substantially no oxygen gas is then sent from the first chamber 151 to the second chamber 152 via the diffusion passage 150. At this moment, the ammeter 292 measures the current flowing in the oxygen pump cell circuit 29. The measured current value is proportional to the pumped oxygen gas amount. Thus, the oxygen gas concentration of the sample gas is measurable from the measured current.

The measuring electrode 311 of the sensor cell 3 is a Pt electrode that has the chemical activity against NOx gas. The voltage of the power supplier 391 is applied between the measuring electrode 311 and the reference electrode 312 of the sensor cell 3. The measuring electrode 311 decomposes the NOx gas into nitrogen ion and oxygen ions. The oxygen ions cause an ion current which flows across the second solid electrolytic member 13 and advances toward the reference gas chamber 16. The ammeter 392 of the sensor circuit 39 measures this ion current. Thus, the NOx gas concentration of the sample gas is measurable from the measured ion current value.

The gas sensing element 1 of the first embodiment functions in the following manner.

The gas sensing element 1 has the introducing passage 100 with the inlet 101 covered by the porous diffusion resistive layer 10.

The sample gas diffuses during it passes through or penetrates the porous diffusion resistive layer 10. This diffusion includes both the Knudsen diffusion and the molecular diffusion. Thus, the caused diffusion is less dependent on the temperature. The diffusion amount of the sample gas introduced into the sample gas chamber 15 is substantially constant irrespective of high or low (or increase or decrease) of the temperature.

As the first embodiment can suppress or eliminate the temperature dependency in the diffusion amount of the sample gas, the sample gas chamber 15 can substantially receive the constant amount of sample gas irrespective of the temperature. Hence, the NOx gas amount in the sample gas chamber 15 is always proportional to the NOx gas concentration of the measuring gas. Thus, it becomes possible to provide the gas sensing element 1 which can suppress or eliminate adverse temperature influence in the measuring accuracy.

Accordingly, the first embodiment provides the gas sensing element which is preferably used in severe circumstances in which the temperature varies widely.

Furthermore, the gas sensing element 1 of the first embodiment satisfies the relationship A/B≦0.5 when "A" represents the distance from the central position 109 of the introducing passage 100 to the front edge 219 of the outside pump electrode 211, and "B" represents the length of the outside pump electrode 211. This is effective to stabilize the offset current which is a sensor current obtained when the NOx gas is absent.

The gas sensing element 1 disclosed in FIGS. 1A and 1B includes the sample gas chamber 15 separated into the first chamber 151 and the second chamber 152. However, it is possible to modify the configuration of the sample gas chamber.

Figure 4B:
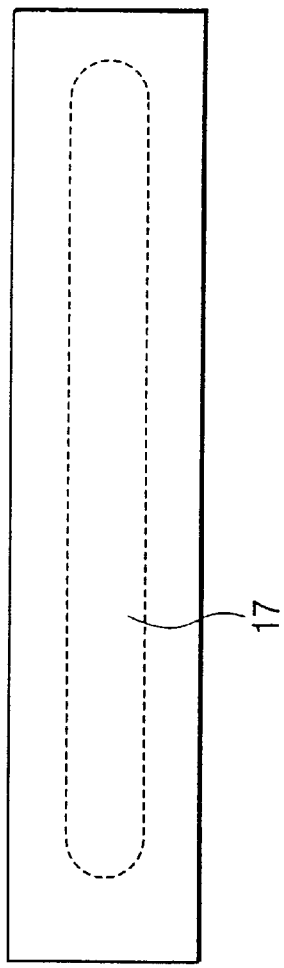
FIG. 4B is a plane view showing an arrangement of the sample gas chamber of the gas sensing element shown in FIG. 4A.

FIGS. 4A and 4B show a modified gas sensing element in accordance with the first embodiment of the present invention, in which only one sample gas chamber 17 is provided.

Hereinafter, the performances of the gas sensing element in accordance with the first embodiment will be explained with reference to the table shown in FIG. 5.

In FIG. 5, samples 1–5 and 8–17 have substantially the same structure as that of the gas sensing element in accordance with the first embodiment of the present invention. The samples 1–5 and 8–17 are different from each other in the dimensions of the introducing passage as well as in the thickness, porosity and pore size of the porous diffusion resistive layer.

Figure 6A:
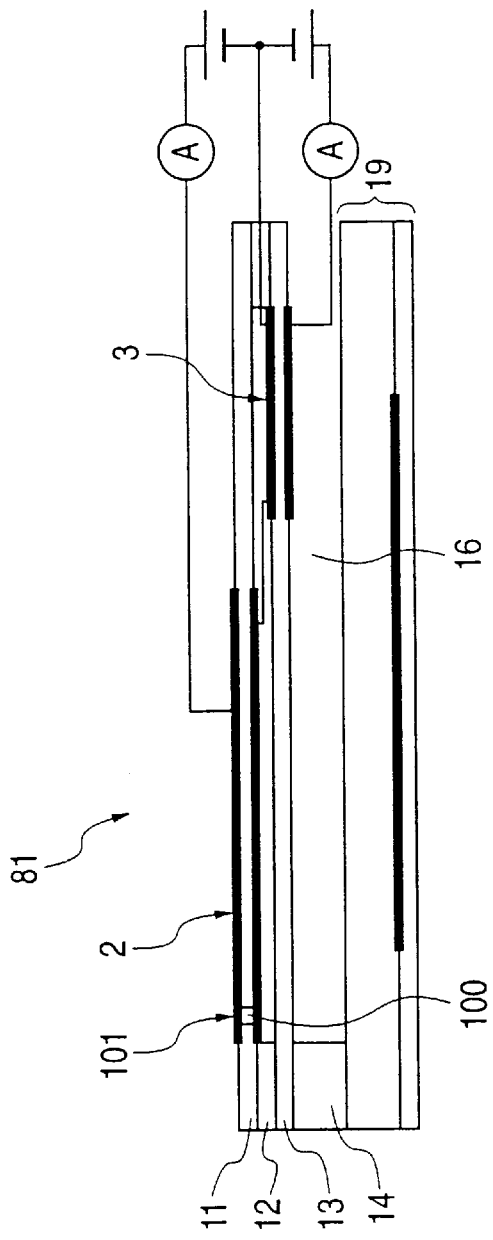
FIG. 6A is a cross-sectional view showing a detailed arrangement of a gas sensing element as a comparative example of the present invention, corresponding to a sample 6 which comprises no porous diffusion resistive layer.
Figure 6B:
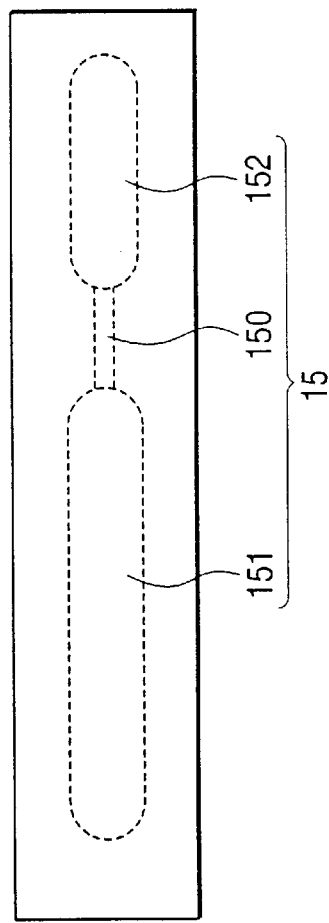
FIG. 6B is a plane view showing an arrangement of a sample gas chamber of the gas sensing element shown in FIG. 6A.

As shown in FIGS. 6A and 6B, sample 6 is a gas sensing element 81 having no porous diffusion resistive layer, although the rest of the structure is substantially identical with that of the above-described gas sensing element of the first embodiment.

Figure 7A:
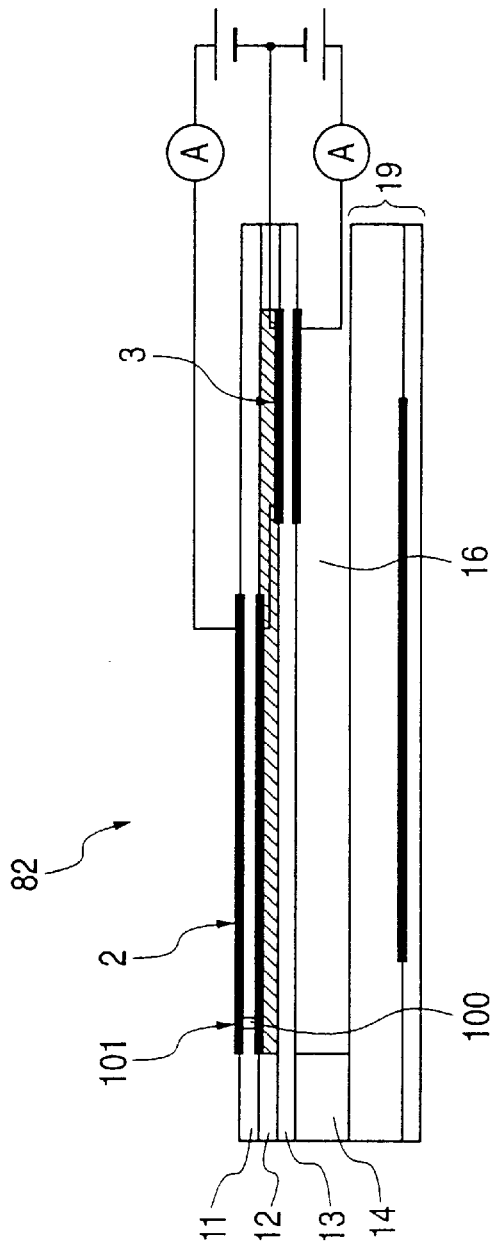
FIG. 7A is a cross-sectional view showing a detailed arrangement of a gas sensing element corresponding to a sample 7 which comprises a sample gas chamber filled with a porous member.
Figure 7B:
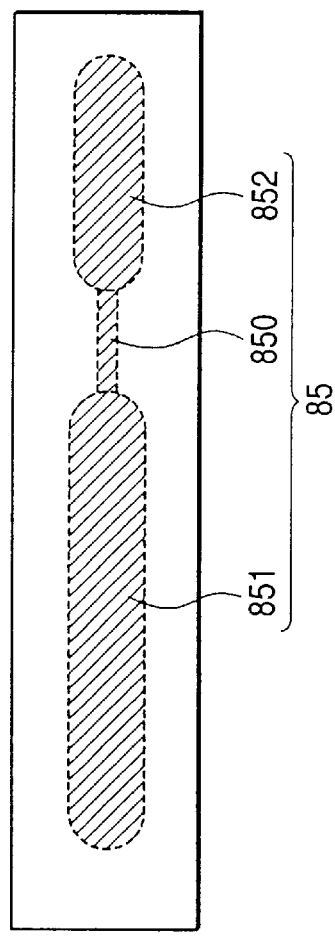
FIG. 7B is a plane view showing an arrangement of the sample gas chamber of the gas sensing element shown in FIG. 7A.
Figure 9A:
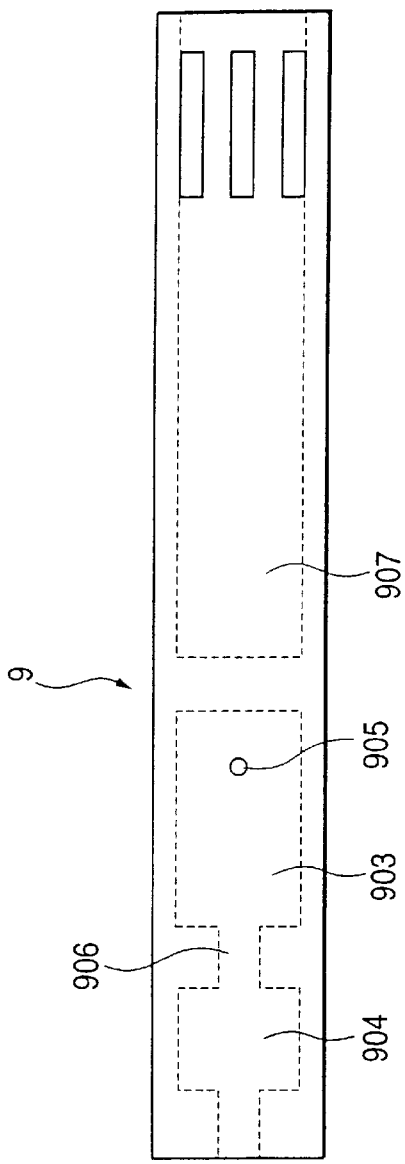
FIG. 9A is a plane view showing a conventional gas sensing element.
Figure 9B:
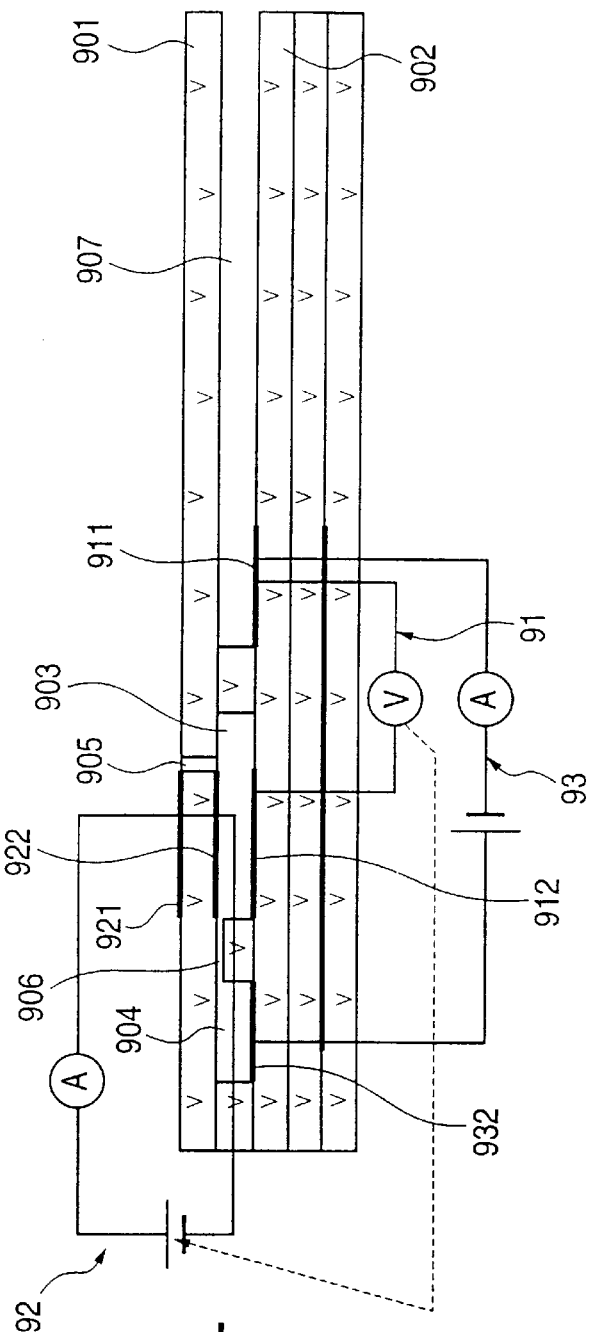
FIG. 9B is a cross-sectional view showing the conventional gas sensing element shown in FIG. 9A.

As shown in FIGS. 7A and 7B, sample 7 is a gas sensing element 82 having a sample gas chamber 85 consisting of a first chamber 851 and a second chamber 852 connected via a diffusion passage 850. The inside space of the sample gas chamber 85 is filled with a porous diffusion resistive member as shown in FIG. 7B. The inlet 101 of the introducing passage 100 is not covered by the porous diffusion resistive member. The rest of the structure is substantially identical with that of the above-described gas sensing element of the first embodiment.

1. Temperature Dependency

A prepared model gas includes a $N_2$-based NO gas (i.e., a type of NOx gas) by the concentration of 1,000 ppm.

Under a condition where the model gas is flowing at a predetermined flow rate (1 liter/min), an output current of each sample (gas sensing element) was measured. More specifically, by using a constant voltage power supplier, a constant voltage (0.5V) was applied to the sensor cell of each element. An ammeter was connected to the sensor cell to measure the output current.

In this case, the temperature of the sensor element was varied in a range of 800±20° C. at the center of its electrode to measure a maximum output and a minimum output. This temperature control was performed by controlling the electric power supplied to the heater integrally formed with the sensor element. When a difference between the maximum output and the minimum output was less than 10%, evaluation for the temperature dependency was indicated by ○ in the table. When the difference between the maximum output and the minimum output was equal to or larger than 10%, evaluation for the temperature dependency was indicated by X in the table.

2. Crack in Sintering

Generation of crack during the sintering process was checked by using a color check. The color check was performed in a region corresponding to the porous diffusion resistive layer and its neighboring solid electrolytic member after the sensing element was sintered. When the crack generation rate was equal to or less than 1%, evaluation for the crack generation was indicated by ○ in the table. When the crack generation rate was larger than 1%, evaluation for the crack generation was indicated by X in the table.

3. Output Current

An output current of each gas sensing element was measured by controlling the gas flow amount in the same manner as in the measurement of the temperature dependency. An output current obtained from the model gas containing 1,000 ppm NOx gas was compared with an output current obtained from a reference gas containing no NOx gas. When the output current difference was equal to or larger than 1 $\mu$A, evaluation for the output current was indicated by ○ in the table. When the output current difference was less than 1 $\mu$A, evaluation for the output current was indicated by X in the table.

4. Oxygen Gas Concentration Dependency

To measure the oxygen gas concentration dependency in the output current of the gas sensing element, the oxygen gas concentration of the model gas was varied in a range from 1 to 20%.

The NO gas concentration of the model gas was adjusted to be 1,000 ppm by adjusting the flow amount. The voltage applied to the pump cell was controlled by using a map controlling circuit. The map control makes it possible to measure the current flowing through the pump cell in advance and apply a voltage corresponding to the measured current. The voltage applied to the gas sensing element was 0.5 V. The output current was measured by an ammeter.

When the fluctuation of the output current was less than ±10% evaluation for the oxygen gas concentration dependency was indicated by ○ in the table. When the fluctuation of the output current was equal to or larger than less than ±10%, evaluation for the oxygen gas concentration dependency was indicated by X in the table.

5. Response

The response of the gas sensing element was measured in the following manner.

The NO gas concentration of the model gas was changed from 1,000 ppm to 100 ppm. During this change, the response was evaluated by a time required for the output current to reduce to 60% of the initial value corresponding to 1,000 ppm NO gas concentration.

When the required time was less than 1 sec, evaluation for the response was indicated by ○ in the table. When the required time was equal to or larger than 1 sec, evaluation for the response was indicated by X in the table.

According to the table shown in FIG. 5, all of the samples having the porous diffusion resistive layer covering the inlet of the introducing passage were evaluated by ○ in the temperature dependency. In other words, the sensor output current was not substantially influenced by the temperature.

On the other hand, the sample 6 has no porous diffusion resistive layer. The output current of the sample 6 varies widely in response to the temperature.

The sample 7 is a gas sensing element having a porous diffusion resistive member in the sample gas chamber. A relatively large number of cracks were generated in the solid electrolytic member during the sintering process of the sample 7, although the temperature dependency of the sample 7 was comparable with those of the samples 1 to 5. It is believed that the thermal expansion difference between the porous diffusion resistive member (alumina) and the solid electrolytic member (zirconia) induces the crack generation.

Furthermore, the sample 7 was relatively insufficient in the output current. It is believed that the porous diffusion resistive member in the sample gas chamber increases the diffusion resistance.

When the sensor output is small, the S/N (signal to noise) ratio may be dissatisfactory and the sensing accuracy of the sensing element may be worsened.

As understood from the table shown in FIG. 5, samples 10, 12, 14 and 16 demonstrated excellent properties in all of the temperature dependency, the crack generation, the output current, the oxygen gas concentration dependency, and the response. In other words, the samples 10, 12, 14 and 16 have preferable values in the dimensions (A/B value, cross section) of the introducing passage as well as in the thickness, porosity and pore size of the porous diffusion resistive layer.

The sample 8 was dissatisfactory in the response. It is believed that the porous diffusion resistive layer is too thick to allow the sample gas to smoothly diffuse across the porous diffusion resistive layer.

The sample 9 has a large value in the ratio of A/B. This is not desirable in that the sample gas reaches the sensor cell before the pump cell sufficiently discharges the oxygen gas. Thus, the output current sensitively varies in response to the oxygen gas concentration. The measuring accuracy may deteriorate when the oxygen gas concentration becomes large.

The sample 13 is large in the cross section of the introducing passage. Thus, the sample 13 allows a large amount of sample gas to enter into the sample gas chamber at a time. It is believed that the oxygen pump cell cannot discharge the oxygen gas sufficiently. Accordingly, the sample 13 was dissatisfactory in the oxygen gas concentration dependency.

The sample 15 is small in both the porosity and the mean pore diameter of the porous diffusion resistive layer. It is believed that a sufficient amount of sample gas cannot pass across the porous diffusion resistive layer. Thus, the sample 15 was dissatisfactory in the output current and the response.

The sample 17 is large in both the porosity and the mean pore diameter of the porous diffusion resistive layer. Thus, the sample 13 allows a large amount of measuring gas to enter into the sample gas chamber at a time. It is believed that the oxygen pump cell cannot discharge the oxygen gas sufficiently. Accordingly, the sample 17 was dissatisfactory in the oxygen gas concentration dependency.

Second Embodiment

A second embodiment is a gas sensing element comprising an oxygen sensor cell in addition to the oxygen pump cell and the sensor cell.

As shown in FIGS. 8A and 8B, the gas sensing element 1' of the second embodiment comprises a sample gas chamber 15, an introducing passage 100 for introducing the measuring gas into the sample gas chamber 15, the sensor cell 3, and the oxygen pump cell 2. Furthermore, the gas sensing element 1 includes an oxygen sensor cell 4 which is capable of measuring the oxygen gas concentration in the sample gas chamber 15.

An inlet 101 of the introducing passage 100 is covered by the porous diffusion resistive layer 10.

More specifically, as shown in FIG. 8A, the gas sensing element 1' of the second embodiment comprises a first solid electrolytic member 11, a first spacer 12 for defining the sample gas chamber 15, a second solid electrolytic member 13, a second spacer 14 for defining a reference gas chamber 16, and a heater 19. These plane members 11 to 14 and 19 are laminated or stacked so as to constitute a multilayered sensing element body.

The oxygen pump cell 2 comprises an inside pump electrode 212 and an outside pump electrode 211 provided on opposite surfaces (i.e., lower and upper surfaces) of the first solid electrolytic member 11. The inside pump electrode 212 faces a first chamber 151 of the sample gas chamber 15. The outside pump electrode 211 faces the outside of the gas sensing element 1.

The sensor cell 3 comprises a measuring electrode 311 and a reference electrode 312 provided on opposite surfaces (i.e., upper and lower surfaces) of the second solid electrolytic member 13. The measuring electrode 311 faces a second chamber 152 of the sample gas chamber 15. The reference electrode 312 faces the reference gas chamber 16 which is defined by the second spacer 14 located adjacent to the second solid electrolytic member 13.

The heater 19 is located next (downside) to the second spacer 14 defining the reference gas chamber 16.

The oxygen sensor cell 4 comprises an electrode 411 provided on the surface of the second solid electrolytic member 13. The other electrode of the oxygen sensor cell 4 is the measuring electrode 311 of the sensor cell 3. In other words, the measuring electrode 311 is commonly used for the sensor cell 3 and for the oxygen sensor cell 4. The electrode 411 and the measuring electrode 311 are positioned in a confronting relationship in the second chamber 152.

Although not shown in FIG. 8A, leads and terminals of the outside pump electrode 211 and the inside pump electrode 212 are provided on the first solid electrolytic member 11. An oxygen pump cell circuit 29 is provided to supply electric power to the oxygen pump cell 2 via the leads and terminals. The oxygen pump cell circuit 29 comprises a power supplier 291 for applying a voltage to the oxygen pump cell 2 and an ammeter 292 for measuring a current in the oxygen pump cell circuit 29.

Similarly, leads and terminals of the measuring electrode 311 and the reference electrode 312 are provided on the second solid electrolytic member 13. A sensing circuit 39 is connected to the leads and terminals of the measuring electrode 311 and the reference electrode 312. The sensing circuit 39 comprises a power supplier 391 for applying a voltage to the sensor cell 3 and an ammeter 392 for measuring a current in the sensing circuit 39.

Similarly, the oxygen sensor cell 4 is connected to a circuit 49 via leads and terminals. The circuit 49 comprises a voltmeter 492.

According to the gas sensing element 1' of the second embodiment, the oxygen pump cell 2 pumps (discharges or introduces) the oxygen gas from or to the first chamber 151 and the sensor cell 3 detects the NOx gas concentration. The voltmeter 492 is used to measure the voltage between the electrode 411 and the electrode 311 so that the oxygen gas can be accurately discharged by the pumping of the oxygen pump cell 2. The caused voltage is an electromotive force expressed by the Nernst equation which is proportional to the oxygen gas concentration in the second chamber 152.

Accordingly, an appropriate feedback control circuit is provided between the circuit 49 and the circuit 29. The power supplier 291 in the circuit 29 is controlled by the feedback control circuit so as to surely perform the pumping operation of the oxygen gas. Thus, the second embodiment of the present invention provides a gas sensing element capable of accurately measuring the NOx gas concentration.

Needless to say, the specific gas measurable by the gas sensing element of the present invention is not limited to NOx gas and oxygen gas. The gas sensing element of the present invention can be used to measure other gases, such as HC and CO. Hence, the present invention provides a gas sensing element capable of accurately measuring the specific gas component even in severe circumstances in which the temperature varies widely.

Third Embodiment

A third embodiment discloses a method for measuring a gas concentration and an arrangement of a used gas sensing element.

Figure 10:
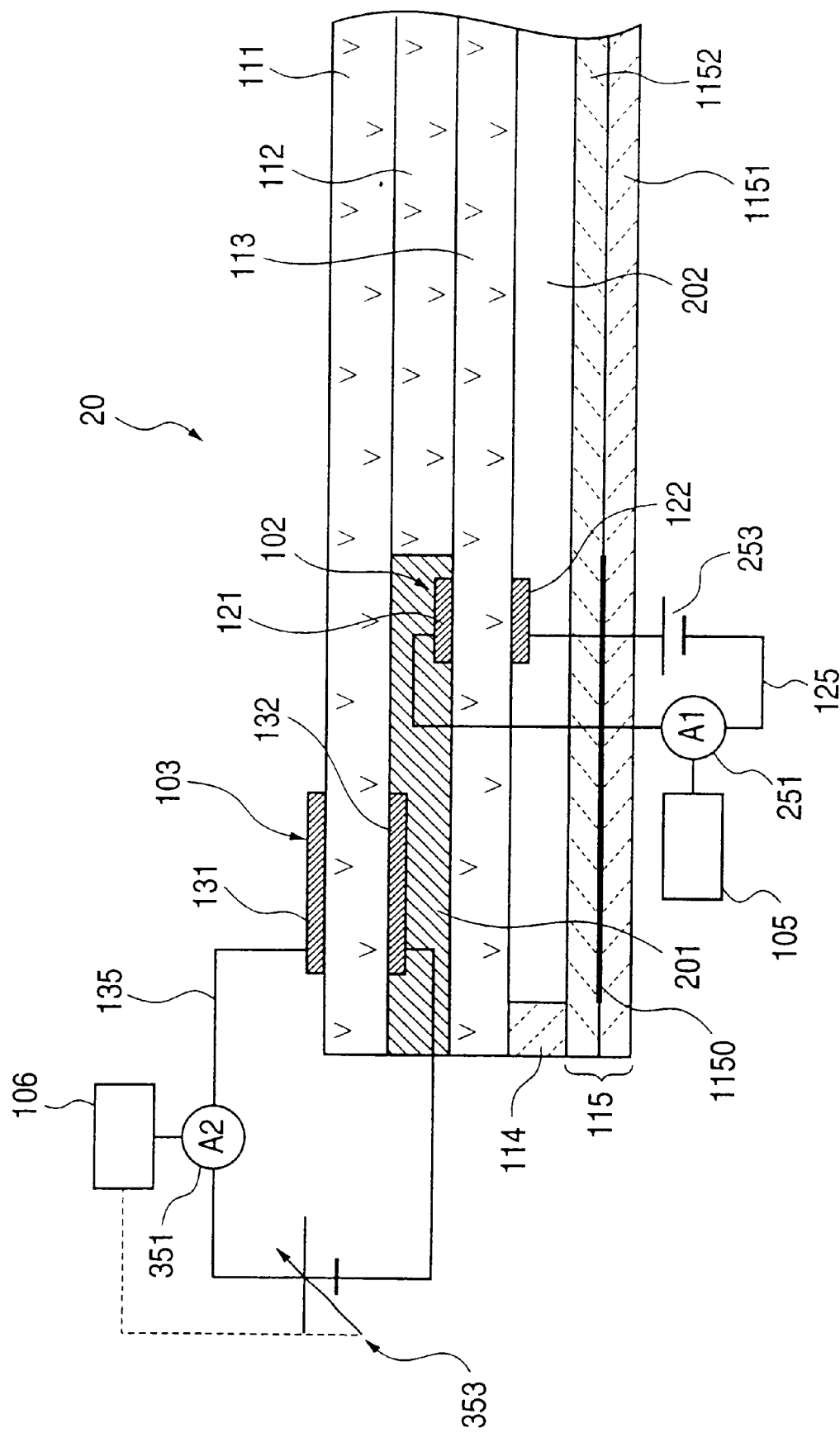
FIG. 10 is a cross-sectional view showing a detailed arrangement of a gas sensing element in accordance with a third embodiment of the present invention.

As shown in FIG. 10, a gas sensing element 20 comprises a sensor cell 102 and a pump cell 103. The sensor cell 102 comprises a measuring electrode 121 and a reference electrode 122 provided on opposite surfaces of a solid electrolytic member 113. The measuring electrode 121 faces a sample gas chamber 201. The reference electrode 122 faces a reference gas chamber 202. The pump cell 103 comprises an outside pump electrode 131 and an inside pump electrode 132 provided on opposite surfaces of another solid electrolytic member 111. The outside pump electrode 131 faces the outside of the gas sensing element 20. the inside pump electrode 132 faces the sample gas chamber 201.

The sensor cell 102 is connected to a sensor circuit 125 comprising a first ammeter 251 and a power supplier 253. The pump cell 103 is connected to a pump circuit 135 comprising a second ammeter 351 and a variable power supplier 353.

The gas sensing element 20 is used to measure an oxygen gas concentration of the measuring gas based on a detected current value of the second ammeter 351. The variable power supplier 353 is controlled based on the measured oxygen gas concentration. Furthermore, the gas sensing element 20 measures a specific gas concentration of the measuring gas based on a detected current value of the first ammeter 251.

The sample gas chamber 201 is constituted by a single chamber which is filled with a porous member.

More specifically, as shown in FIG. 10, the gas sensing element 20 of the third embodiment is a multilayered sensing element which includes a plurality of solid electrolytic members 111 to 113, a spacer 114 and a heater 115 stacked or laminated.

A pair of (i.e., outside and inside) pump electrodes 131 and 132 are provided on the opposite surfaces of the solid electrolytic member 111. The lower pump electrode 132 faces the sample gas chamber 201. The sample gas chamber 201 is surrounded by the solid electrolytic members 111, 112 and 113. The porous member filling this sample gas chamber 201 has a porosity of 12%. The porous member provides an appropriate diffusion resistance against the measuring gas introduced into the sample gas chamber 201. The sample gas diffuses through this porous member when it reaches the measuring electrode 121 of the sensor cell 102 or the lower electrode 132 of the pump cell 103.

The measuring electrode 121 and the reference electrode 122 are provided on the opposite surfaces of the solid electrolytic member 113. The measuring electrode 121 is a Pt (platinum) electrode which decomposes the NOx gas into nitrogen ions and oxygen ions when an appropriate voltage is applied to the sensor cell 102. The oxygen ions cause an ion current which flows across the solid electrolytic member 113 and advances toward the reference gas chamber 202. Namely, the measuring electrode 121 has the chemical activity against NOx gas. Similarly, the reference electrode 122 is a Pt electrode, although it is possible to constitute the reference electrode 122 by using a Au—Pt electrode.

Each of the pump electrodes 131 and 132 is a Au—Pt electrode which does not decompose the NOx gas. The pump cell 103 functions as a means for pumping the oxygen ions in a direction advancing from the sample gas chamber 201 to the outside or in an opposite direction when an appropriate voltage is applied to the pump cell 103.

Figure 11:
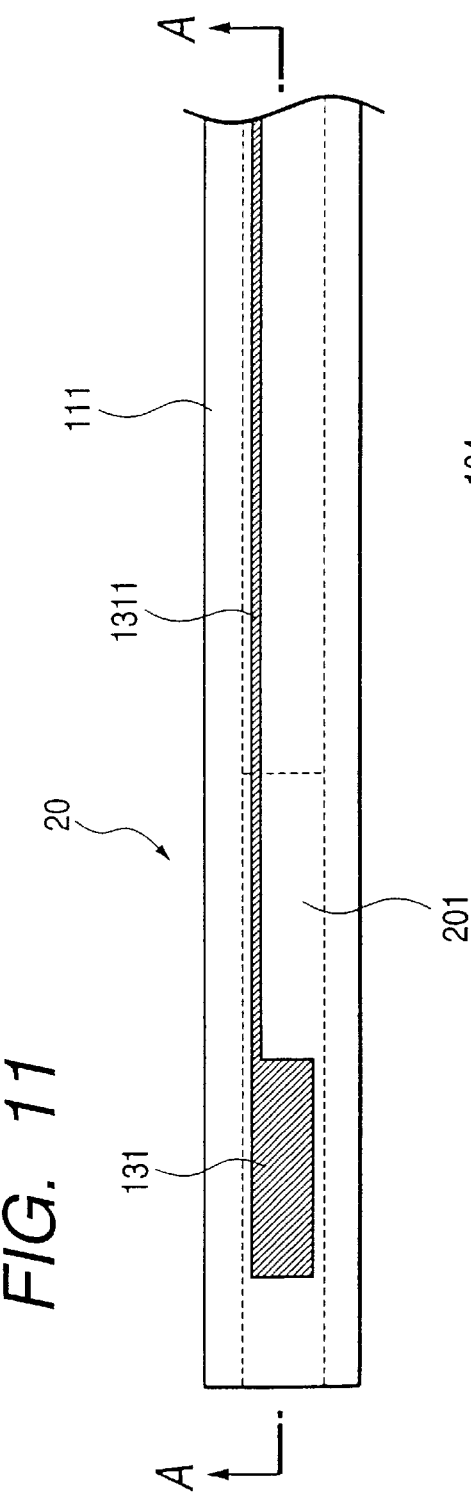
FIG. 11 is a plane view showing the gas sensing element in accordance with the third embodiment of the present invention.

Furthermore, as shown in FIG. 11, the pump cell .103 has a lead 1311 connected to the pump electrode 131. The voltage of the pump cell 103 is applied via this lead 1311. Although not shown in FIGS. 10 and 11, the other pump electrode 132, the measuring electrode 121 and the reference electrode 122 have leads and terminals for applying voltages or outputting detection signals.

The heater 115 is provided next to the spacer 114. The reference gas chamber 202 is surrounded by the solid electrolytic member 113, the spacer 114 and the heater 115. The heater 115 comprises a heater substrate 1151, a shielding substrate 1152, and a heat generating member 1150 sandwiched between these substrates 1151 and 1152. The heat generating member 1150 is a platinum containing member. Although not shown in the drawing, the heater 115 is equipped with leads for supplying electric power to the heat generating member 1150. When seen in the direction normal to the surfaces of the solid electrolytic members 111–114, it is preferable that the heater generating member 1150 extends in an area covering all of the measuring electrode 121, the reference electrode 122, and the pump electrodes 131 and 132.

Each of the electrodes 121, 122, 131 and 132 starts the pumping operation and also decomposes the NOx gas after the temperature increases up to a predetermined level (i.e., activation temperature). Thus, it is important to effectively arrange the heater 115 to quickly warm up all of these electrodes 121, 122, 131 and 132.

Next, the manufacturing method of the gas sensing element 20 will be described.

First, green zirconic sheets for the solid electrolytic members 111, 112 and 113 are manufactured in the following manner.

A powder of 94 mol % zirconia is mixed with a powder of 6 mol % yttria to obtain a yttria partially stabilized zirconia having a mean grain size of 0.5 $\mu$m. Then, the resultant yttria partially stabilized zirconia (100 weight part) is mixed with the materials of $\alpha$-alumina (1 weight part), PVB (5 weight part), DBP (10 weight part), ethanol (10 weight part) and toluene (10 weight part) to obtain a ceramic mixture. PVB is polyvinyl butyral, and DBP is dibutyl phthalate.

Then, a slurry of the prepared ceramic mixture is formed in a ball mill. The resultant slurry is dried by using the doctor blade method to obtain a green zirconic sheet having a thickness of 0.3 mm in a dried condition.

A green zirconic sheet is cut into a rectangular shape of 5 mm×70 mm. A paste, including 1–10 wt % Au added platinum and 10 wt % zirconia, is applied on a surface of the green zirconic sheet by the screen printing method to form the print pattern for the pump electrode 132. Then, another paste including 10 wt % zirconia added platinum is applied on the opposite surface of the same green zirconic sheet by the screen printing method to form the print patterns for the remaining pump electrode 131. The print patterns of the leads connected to the pump electrodes 131 and 132 are similarly formed by using the 10 wt % zirconia added platinum paste. Thus, a green zirconic sheet for the solid electrolytic member 111 is obtained.

Another green zirconic sheet is cut into a U-shape rectangular configuration with an outer periphery of 5 mm×70 mm and an inner cutout periphery of 2 mm×15 mm, thereby obtaining a green zirconic sheet for the solid electrolytic member 112.

Another green zirconic sheet is cut into a rectangular shape of 5 mm×70 mm. A print pattern for the measuring electrode 121 is formed on a surface of this green zirconic sheet by using the 10 wt % zirconia added platinum paste. Furthermore, print patterns for the reference electrode 122 and the leads connected to these electrodes 121 and 122 are similarly formed by using the 10 wt % zirconia added platinum paste.

Next, green alumina sheets for the spacer 114, the heater substrate 1151 and the shielding substrate 1152 are manufactured in the following manner.

A powder of α-alumina having a mean grain size of 0.3 μm (98 weight part) is mixed with the 6 mol % yttria partially stabilized zirconia (3 weight part), PVB (10 weight part), DBP (10 weight part), ethanol (30 weight part) and toluene (30 weight part) to obtain a ceramic mixture. Then, a slurry of the prepared ceramic mixture is formed in the ball mill. The resultant slurry is dried by using the doctor blade method to obtain a green alumina sheet having a thickness of 0.3 mm in a dried condition.

An obtained green alumina sheet is cut into a U-shape rectangular configuration with an outer periphery of 5 mm×70 mm and an inner closed periphery of 2 mm×65 mm, thereby obtaining a green alumina sheet for the spacer 114.

Another green alumina sheet is cut into a rectangular shape of 5 mm×70 mm. A paste, including 90 wt % Pt and 10 wt % alumina, is applied on a surface of this green alumina sheet by the screen printing method to form print patterns for the heat generating member 1150 and the associated leads. Thus, a green alumina sheet for the heater substrate 1150 is obtained.

Furthermore, a green alumina sheet for the shielding substrate 1152 is obtained by cutting the green alumina sheet into a rectangular shape of 5 mm×70 mm.

Next, a method for manufacturing the porous member filling the sample gas chamber 201 will be explained.

An alumina paste is used to form the porous member.

PVB (10 weight part) serving as a binder, DBP (5 weight part) serving as a plasticizer, Span 85-sorbitan triolate (1 weight part) serving as an antifoaming agent, terpineol (50 weight part) serving as a solvent, and alumina powder (100 weight part) are mixed together and processed 20 times in a three roll mill to obtain the alumina paste.

The produced green sheets are laminated or put one on another in the following manner.

First, the green zirconic sheet for the solid electrolytic member 112 and the green zirconic sheet for the solid electrolytic member 113 are integrated by a thermo-compression bonding method. Next, the hollow space of the solid electrolytic member 112 is filled with the above alumina paste by the screen printing method, thereby forming the sample gas chamber 201.

Then, as shown in FIG. 10, the remaining green sheets are successively laminated together with the above green sheets by the thermo-compression bonding method, thereby forming a multilayered sensing body. The resultant multilayered sensing body is sintered in the air at the temperature of 1,500° C. for one hour. Thus, the gas sensing element 20 of the third embodiment is obtained.

Next, a method for measuring a specific gas component and an oxygen gas concentration by using the gas sensing element 20 will be explained.

Figure 12:
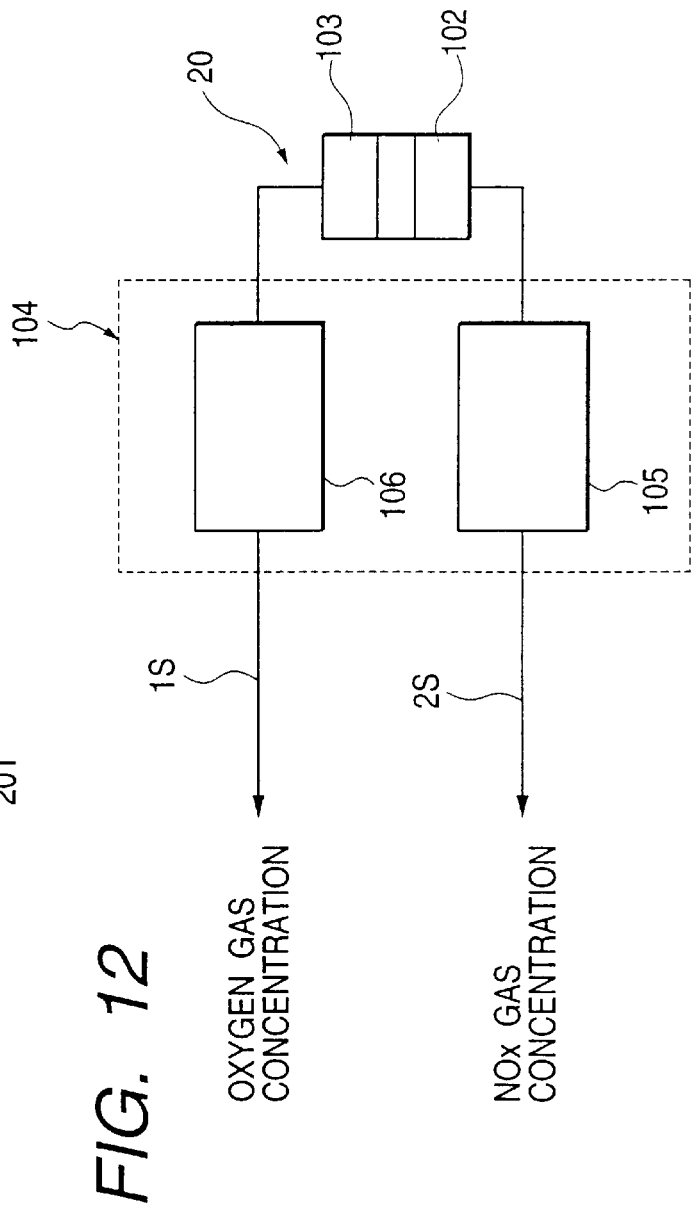
FIG. 12 is a schematic block diagram showing a measuring system for the gas sensing element of the third embodiment of the present invention.

As shown in FIG. 12, the gas sensing element 20 is associated with a control circuit 104 which comprises an oxygen gas concentration detecting means 106 connected to the pump cell 103 and a specific gas concentration detecting means 105 connected to the sensor cell 102. The oxygen gas concentration detecting means 106 generates a signal 1S representing an oxygen gas concentration. The specific gas concentration detecting means 105 generates a signal 2S representing a NOx gas concentration.

Figure 13:
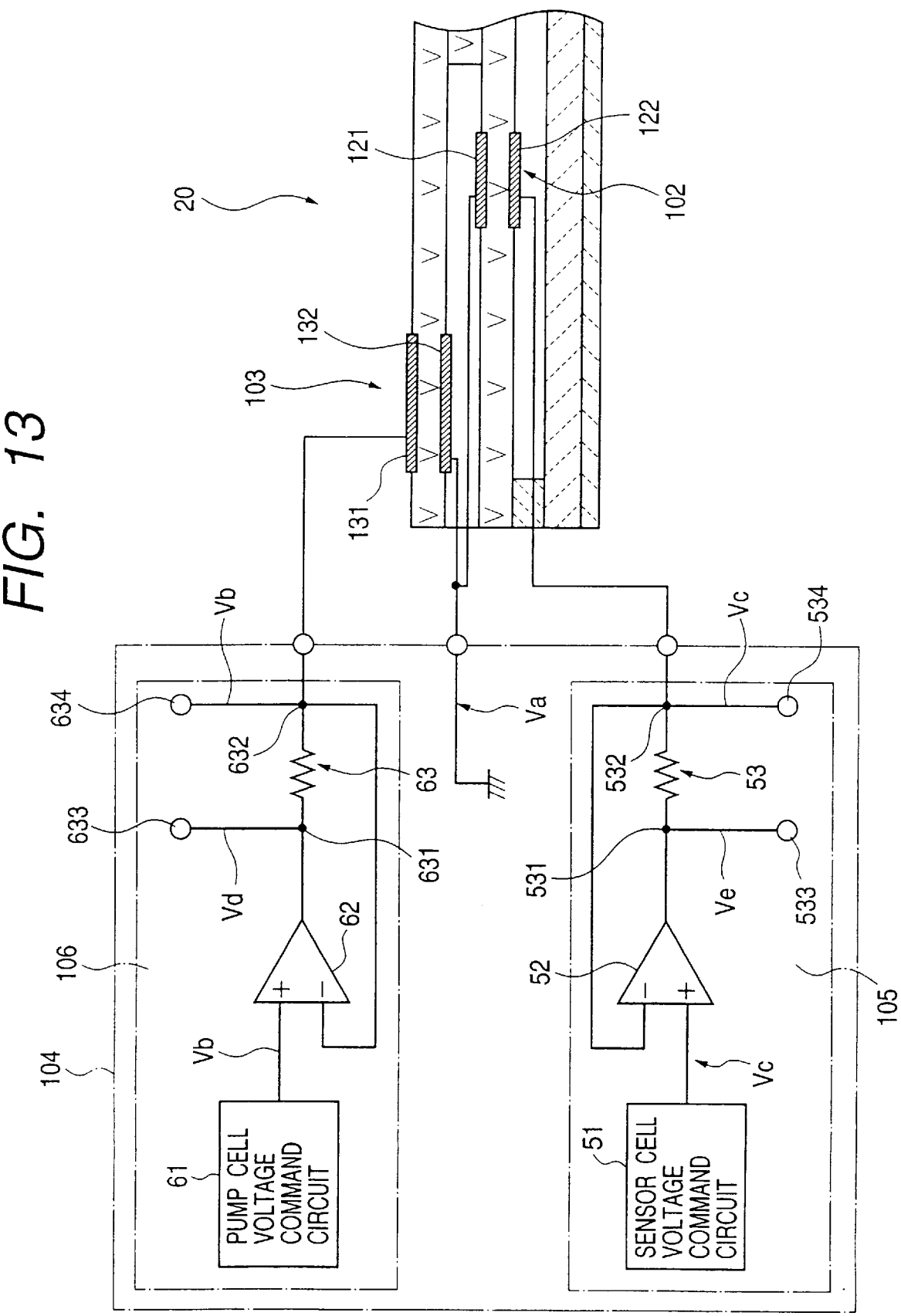
FIG. 13 is a circuit diagram showing a detailed arrangement of the measuring system shown in FIG. 12.

FIG. 13 shows a detailed arrangement of the control circuit 104. The pump electrode 132 and the measuring electrode 121 are both grounded. In other words, the pump electrode 132 and the measuring electrode 121 are maintained at a common potential Va. The oxygen gas concentration detecting means 106 comprises a pump cell voltage command circuit 61, an amplification circuit 62, and a resistor 63. The pump cell voltage command circuit 61 generates a command voltage Vb to control a voltage applied to the pump cell 103. The amplification circuit 62 has a non-inverting input terminal receiving the command voltage Vb from the pump cell voltage command circuit 61. The resistor 63 is used to detect a pump cell current responsive to the oxygen gas concentration.

An output terminal of the amplification circuit 62 is connected to one end 631 of the resistor 63. A terminal 633, for detecting the current responsive to the oxygen gas concentration, is also connected to the terminal 631 of the resistor 63. Vd represents a voltage level of the terminal 633.

The other end 632 of the resistor 63 is connected to the pump electrode 131 of the gas sensing element 20. The terminal 632 of the resistor 63 is also connected to an inverting input terminal of the amplification circuit 62 and to a terminal 634 which detects the current responsive to the oxygen gas concentration. The terminal 634 has the same potential as the command voltage Vb supplied from the pump cell voltage command circuit 61.

Accordingly, the command voltage Vb is generated from the pump cell voltage command circuit 61 and applied to the pump cell 103. The pump cell current responsive to the oxygen gas concentration flows through the resistor 63. The pump cell current is measurable based on a voltage difference between Vd and Vb according to the following equation.

$$\text{Pump Cell Current } I_p = (V_d - V_b)/R63$$

where R63 represents a resistance value of the resistor 63. The obtained pump cell current represents the oxygen gas concentration.

The specific gas concentration detecting means 105 comprises a sensor cell voltage command circuit 51, an amplification circuit 52, and a resistor 53. The sensor cell voltage command circuit 51 generates a command voltage Vc to control a voltage applied to the sensor cell 102. The amplification circuit 52 has a non-inverting input terminal receiving the command voltage Vc from the sensor cell voltage command circuit 51. The resistor 53 is used to detect a sensor cell current responsive to the NOx gas concentration.

An output terminal of the amplification circuit 52 is connected to one end 531 of the resistor 53. A terminal 533, for detecting the current responsive to the NOx gas concentration, is also connected to the end 531 of the resistor 53. Ve represents a voltage level of the terminal 533.

The other end 532 of the resistor 53 is connected to the reference electrode 122 of the gas sensing element 20. The terminal 532 of the resistor 53 is also connected to an inverting input terminal of the amplification circuit 52 and to a terminal 534 which detects the current responsive to the NOx gas concentration. The terminal 534 has the same potential as the command voltage Vc supplied from the sensor cell voltage command circuit 51.

Accordingly, the command voltage Vc is generated from the sensor cell voltage command circuit 51 and applied to the sensor cell 102. The sensor cell current responsive to the NOx gas concentration flows through the resistor 53. The sensor cell current is measurable based on a voltage difference between Ve and Vc according to the following equation.

$$\text{Sensor Cell Current } Is=(Ve-Vc)/R53$$

where R53 represents a resistance value of the resistor 53. The obtained sensor cell current represents the NOx gas concentration.

Figure 15:
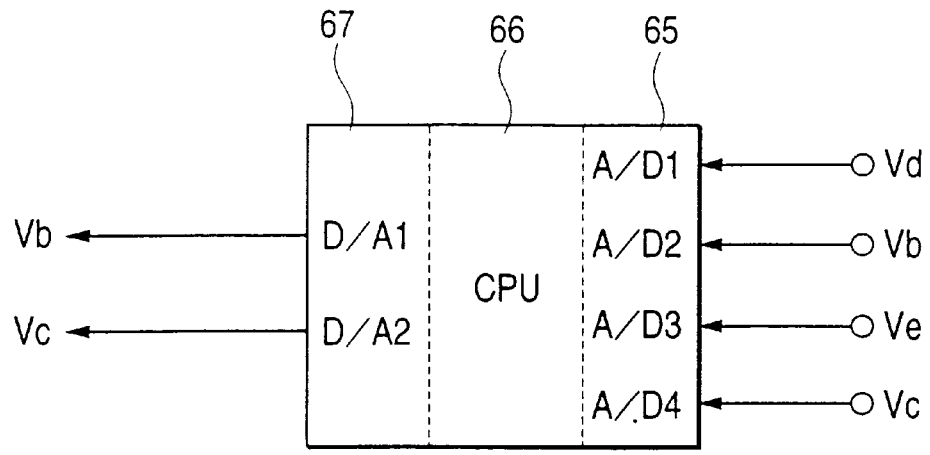
FIG. 15 is a schematic block diagram of the measuring system including a microcomputer in accordance with the third embodiment of the present invention.

As shown in FIG. 15, the pump cell voltage command circuit 61 and the sensor cell voltage command circuit 51 are practically realized by a microcomputer 66, an A/D converter 65, and a D/A converter 67.

Figure 14:
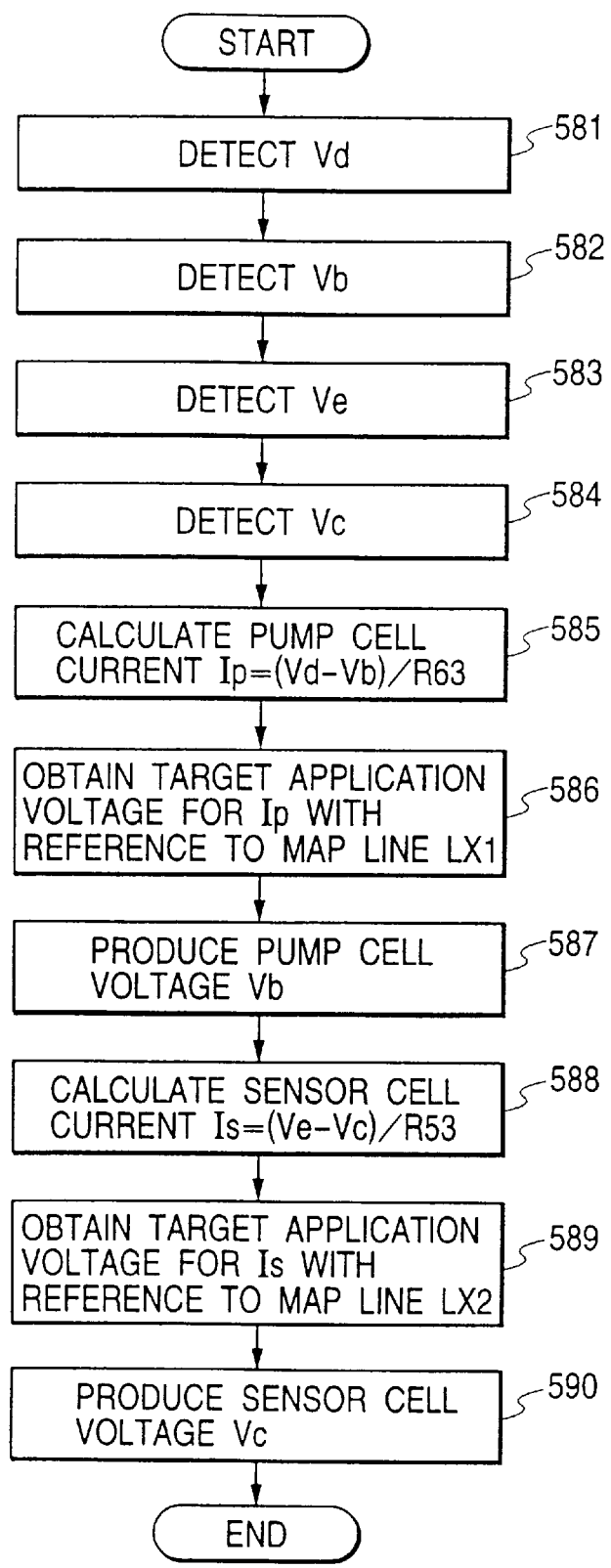
FIG. 14 is a flowchart showing a control procedure for detecting an oxygen concentration and a specific gas concentration in accordance with the third embodiment of the present invention.

FIG. 14 is a flowchart showing a detailed operation of the pump cell voltage command circuit 61 and the sensor cell voltage command circuit 51.

Steps 581 and 582 detect terminal voltages Vd and Vb at the terminals 631 and 632 of the resistor 63 which detects the current flowing through the pump cell 103. More specifically, as shown in FIGS. 13 and 15, the voltage Vd of one terminal 631 of the resistor 63 is input to the analog-to-digital converter A/D1. The microcomputer 66 reads the digital data corresponding to Vd which is produced from the converter A/D1. Similarly, the voltage Vb of the other terminal 632 of the resistor 63 is input to the analog-to-digital converter A/D2. The microcomputer 66 reads the digital data corresponding to Vb produced from the converter A/D2.

Steps 583 and 584 detect terminal voltages Ve and Vc at the terminals 531 and 532 of the resister 53 which detects the current flowing through the sensor cell 102. More specifically, the voltage Ve of one terminal 531 of the resistor 53 is input to the analog-to-digital converter A/D3. The microcomputer 66 reads the digital data corresponding to Ve which is produced from the converter A/D3. Similarly, the voltage Vc of the other terminal 532 of the resistor 53 is input to the analog-to-digital converter A/D4. The microcomputer 66 reads the digital data corresponding to Vc produced from the converter A/D4.

Step 585 calculates the pump cell current Ip based on the detected values of the terminal voltages Vd and Vb and the resistance value R63 of the resistor 63.

Step 586 obtains a target application voltage for obtaining the calculated pump cell current Ip with reference to an application voltage line LX1 shown in FIG. 16. Namely, the target application voltage for the pump cell 103 is obtained through a map calculation.

FIG. 16 shows voltage-current characteristic curves of the pump cell corresponding to various oxygen gas concentration values, wherein the ordinate (i.e., vertical axis) represents the pump cell current Ip and the abscissa (i.e., lateral axis) represents the pump cell application voltage. The application voltage line LX1 is a straight line connecting the midpoints of flat regions (limit-current regions) in respective voltage-current characteristic curves ① to ⑤ corresponding to different oxygen gas concentration values. In practice, the sample gas includes a small amount of NOx gas in addition to the oxygen gas. Thus, the target application voltage should be determined at a region where no decomposition of NOx gas occurs.

Step 587 outputs the obtained target application voltage for the pump cell 103 through the digital-to-analog converter D/A1 as a renewed command voltage Vb.

Next, step 588 calculates the sensor cell current Is based on the detected values of the terminal voltages Ve and Vc and the resistance value R53 of the resistor 53.

Step 589 obtains a target application voltage for obtaining the calculated sensor cell current Is with reference to an application voltage line LX2 shown in FIG. 17. Namely, the target application voltage for the sensor cell 102 is obtained through a map calculation.

FIG. 17 shows voltage-current characteristic curves of the sensor cell corresponding to various NOx gas concentration values, wherein the ordinate (i.e., vertical axis) represents the sensor cell current Is and the abscissa (i.e., lateral axis) represents the sensor cell application voltage. The application voltage line LX2 is a straight line connecting the midpoints of flat regions in respective voltage-current characteristic curves ① to ③ corresponding to different NOx gas concentration values.

Step 590 outputs the obtained target application voltage for the sensor cell 102 through the digital-to-analog converter D/A2 as a renewed command voltage Vc.

In this manner, the gas sensing element 20 of the third embodiment measures both the oxygen gas concentration and the NOx gas concentration.

The gas sensing element of the third embodiment operates in the following manner.

As understood from FIG. 16, the pump cell current increases in proportion to the applied voltage when the application voltage value is small. When the applied voltage reaches a predetermined level, the pump cell current stops increasing irrespective of change of the applied voltage. This region is referred to as a limit-current region. When the applied voltage increases to a further higher level, the pump cell current restarts increasing in proportion to the applied voltage. As shown in FIG. 16, the voltage-current characteristic curve shifts along an oblique line ascending in the right direction in response to the oxygen gas concentration.

Accordingly, an adjusted voltage is applied to the pump cell 103 from the variable power supplier 353 based on a measured current of the second ammeter 351 so that the limit current flows through the pump cell 103. The oxygen gas is discharged out of the sample gas chamber 201 so as to adjust the air-fuel ratio in the sample gas chamber to a theoretical (i.e., stoichiometric) value. Accordingly, the oxygen amount in the sample gas chamber is maintained at a constant value of approximately $1 \times 10^{-6}$ atm.

As the limit-current value is proportional to the oxygen gas concentration, the pump circuit 135 can be used to measure the oxygen gas concentration contained in the measuring gas introduced into the sample gas chamber.

The power supplier 253 in the sensor circuit 125 applies the voltage to the sensor cell 102. The sensor circuit 125 includes the first ammeter 251.

The specific gas (NOx gas) contained in the sample gas is deoxidized on the measuring electrode in response to the voltage applied to the sensor cell. As the voltage is applied between the measuring electrode and the reference electrode, the produced oxygen ions cause an ion current flowing across the solid electrolytic member of the sensor cell as a current representing the specific gas component contained in the sample gas.

The ion current flows in the sensor circuit connected to the sensor cell. The first ammeter measures the ion current. As shown in FIG. 17, the ion current varies in accordance with the specific gas concentration. Thus, it is possible to measure the specific gas concentration based on a measured current value of the first ammeter.

Furthermore, as described above, almost all of the oxygen gas residing in the sample gas chamber is discharged in advance by the pump electrode. It is therefore believed that all of the oxygen ions ionized on the sensor cell derive from the deoxidization of the specific gas. Thus, it is possible to measure the specific gas concentration based on the measured current value of the first ammeter.

In this manner, the third embodiment provides the method for measuring both the specific gas concentration and the oxygen gas concentration by using only the pump cell and the sensor cell. Thus, the third embodiment provides a gas concentration measuring method realized by a simplified sensing element structure.

Furthermore, the gas sensing element 20 used in the third embodiment has only one sample gas chamber 201 which is filled with the porous member. This porous member has a porosity of 3 to 30%. Maintaining the configuration of the sample gas chamber 201 is easy during the manufacturing process or in use of the gas sensing element. The gas sensing element is thus free from deformation or size error. In each sensing element, the characteristics deviation is minimized. The manufacturing cost is reduced. And, the manufacturing process is simplified. As the sample gas chamber 201 has a firm configuration, the third embodiment makes it possible to provide a gas sensing element having higher measuring accuracy.

The sample gas diffuses in the porous member filling the sample gas chamber 201. In this case, the diffusion of the sample gas includes both the Knudsen diffusion and the molecular diffusion. Thus, temperature dependency of the sensor output is suppressed within an appropriate level.

According to the gas sensing element 20 of the third embodiment, both the measuring electrode 121 of the sensor cell 102 and the pump cell 132 of the pump cell 103 directly face the sample gas chamber 201.

When the gas sensing element is used to measure the NOx gas, the measuring electrode has the chemical activity against NOx gas and the pump electrode has no chemical activity against NOx gas. Thus, the pump electrode 132 contains inactivating additives. However, even when such inactivating additives volatilize, this component remains near the pump electrode 132 without reaching the measuring electrode 121. In other words, the measuring electrode 121 is not contaminated by such volatile additives. Accordingly, the third embodiment of the present invention provides a gas sensing element having excellent measuring accuracy.

Fourth Embodiment

The fourth embodiment discloses another circuit arrangement for the gas sensing element 20. This circuit includes no microcomputer.

Figure 18:
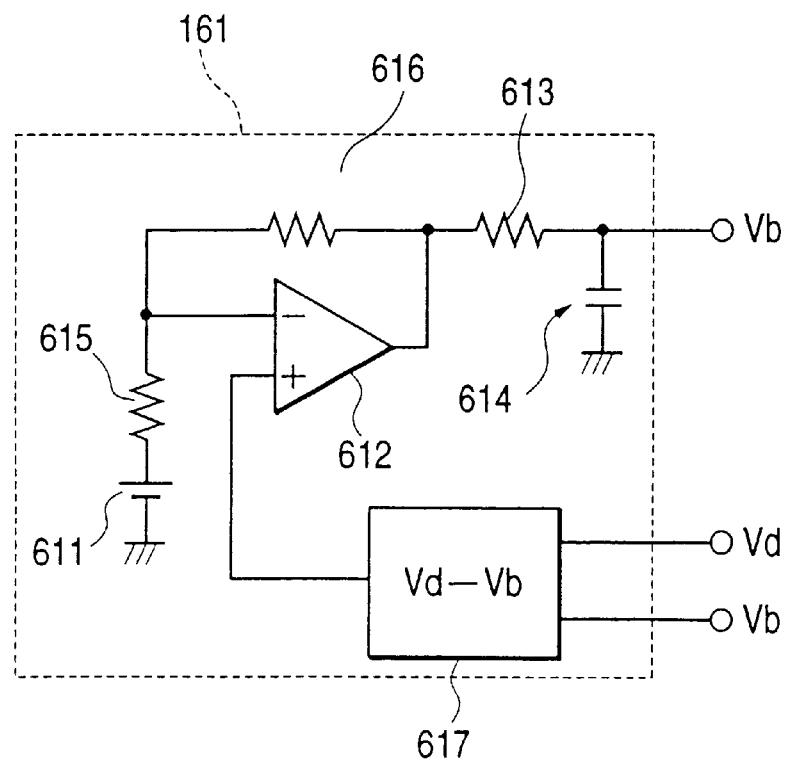
FIG. 18 is a circuit diagram showing a measuring circuit in accordance with a fourth embodiment of the present invention.

As shown in FIG. 18, a pump cell voltage command circuit 161 includes a reference voltage supplier 611, an amplification circuit 612, a pair of resistors 615 and 616, a resistor 613 and a capacitor 614, and a circuit 617. The resisters 615 and 616 determine an amplification factor of the amplification circuit 612. The combined resistor 613 and capacitor 614 cooperatively constitute a low-pass filter. The circuit 617 detects a pump cell current.

The circuit 617 has two input terminals connected to the terminals 633 and 634, respectively. As shown in FIG. 13, the terminals 633 and 634 are connected to both ends of resistor 63 which detects the pump cell current. The circuit 617 has an output terminal which produces a voltage difference (Vd−Vb). The output terminal of the circuit 617 is connected to a non-inverting input terminal of the amplification circuit 612.

An inverting input terminal of the amplification circuit 612 is connected to a joint point of one end of the resistor 615 and one end of the resistor 616. An output terminal of the amplification circuit 612 is connected to a joint point of one end of the resistor 616 and one end of the resistor 613.

The reference voltage supplier 611 applies a reference voltage to the other end of the resistor 615. The other end of the resistor 613 is connected to one end of the capacitor 614 at a joint point which produces a pump command voltage Vb. The other end of the capacitor 614 is grounded.

In this manner, the circuit 617 produces the voltage difference (Vd−Vb) corresponding to the pump cell current. The amplification circuit 612 compares the voltage value of the reference voltage supplier 611 and the pump cell current value (Vd−Vb) and produces an amplified output based on the amplification factor defined by the resistors 615 and 616.

As a result, the application voltage line LX1 is obtained as shown in FIG. 16. The reference voltage supplier 611 produces an offset voltage for the application voltage line LX1 (i.e., an application voltage corresponding to 0 mA). The inclination of the application voltage line LX1 is determined by the amplification circuit 612 and the resistors 615 and 616.

The low-pass filter, consisting of the resistor 613 and the capacitor 614, provides a positive feedback to prevent the produced application voltage from oscillating.

A circuit for generating a sensor cell voltage command can be constituted by using a similar circuit arrangement.

Fifth Embodiment

Figure 19:
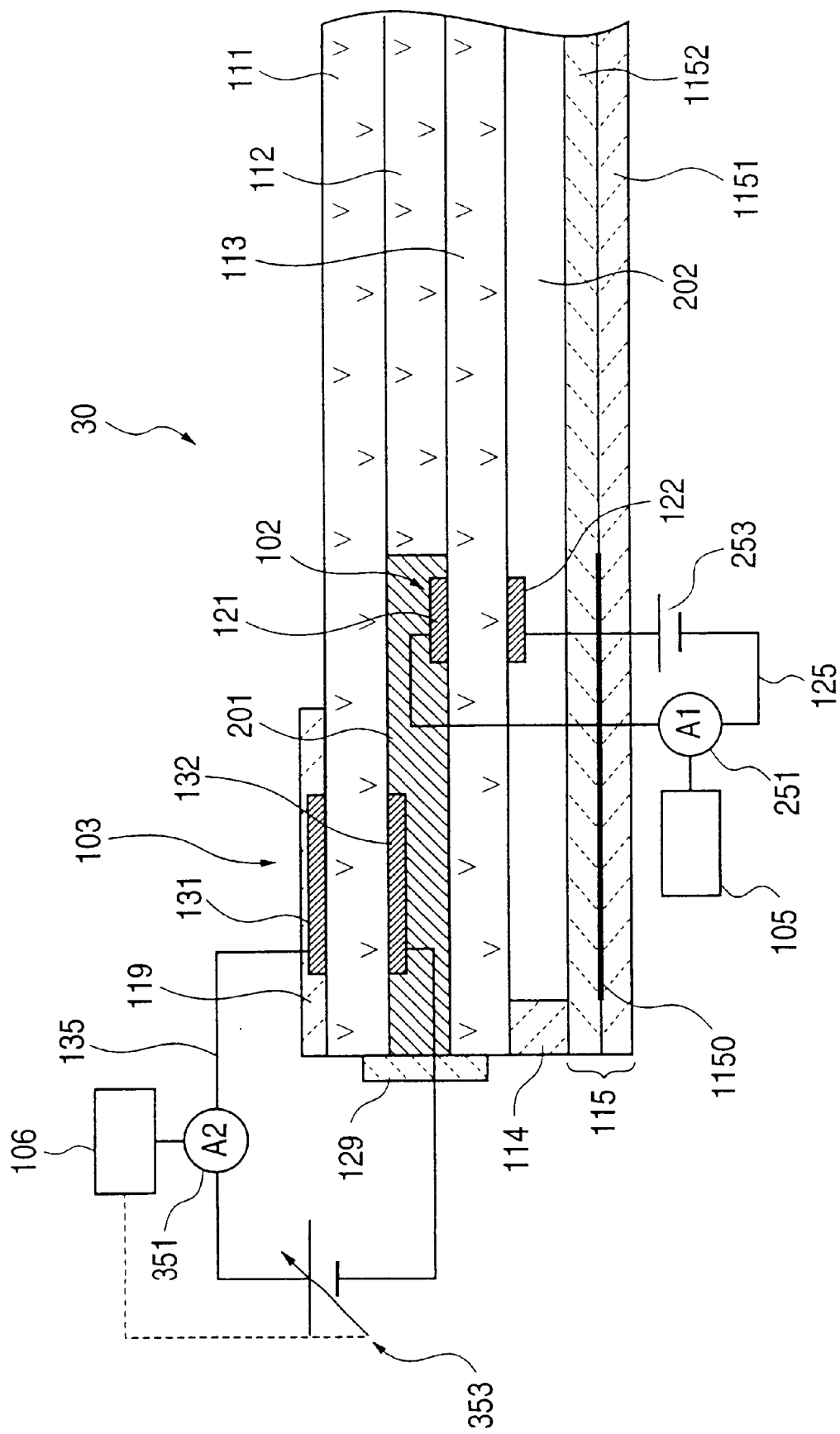
FIG. 19 is a cross-sectional view showing a detailed arrangement of a gas sensing element in accordance with a fifth embodiment of the present invention.

FIG. 19 shows a gas sensing element in accordance with a fifth embodiment of the present invention.

A gas sensing element 30 of the fifth embodiment comprises a protective layer 119 covering the entire surface of the pump electrode 131. The protective layer 119 prevents the pump electrode 131 from being directly subjected to high-temperature exhaust gas. According to the arrangement of gas sensing element 30, the exhaust gas is introduced from the side surface of the sample gas chamber 201. The gas sensing element 30 comprises a trap layer 129 covering the entire side wall of the gas sensing element 30. The trap layer 129 protects the porous member filling the sample gas chamber 201 against poisonous substances contained in the measuring gas.

The rest arrangement of the gas sensing element 30 is identical with that of the gas sensing element 20 shown in FIG. 10.

Sixth Embodiment

Figure 20:
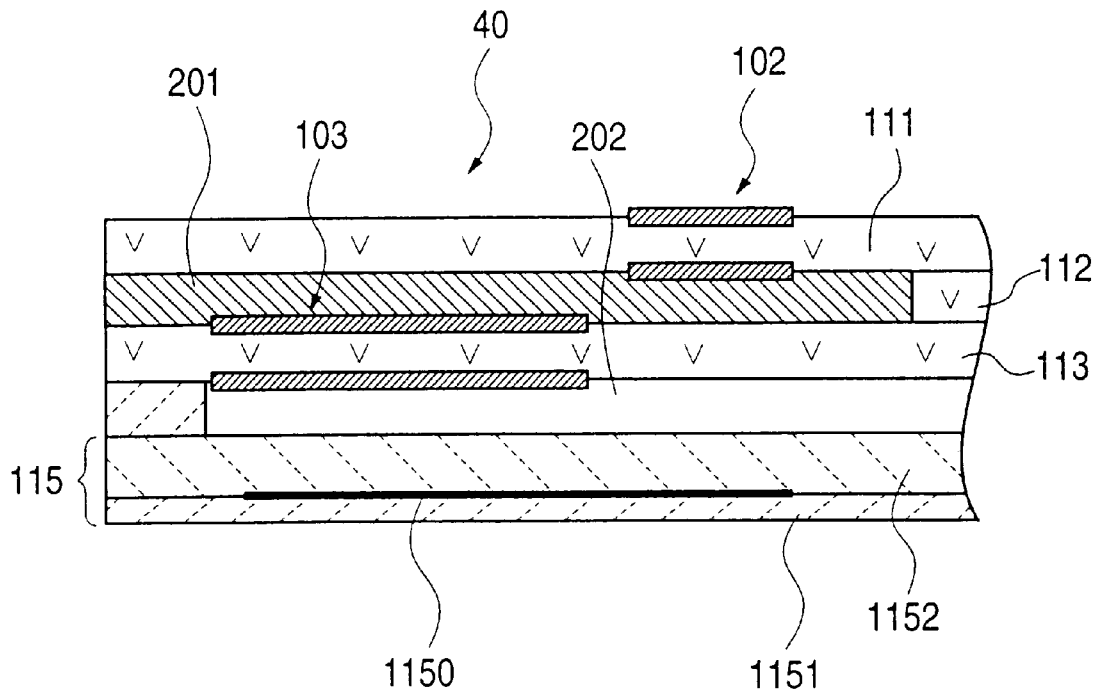
FIG. 20 is a cross-sectional view showing a detailed arrangement of a gas sensing element in accordance with a sixth embodiment of the present invention.

FIG. 20 shows a gas sensing element in accordance with a sixth embodiment of the present invention.

A gas sensing element 40 of the sixth embodiment differs from the gas sensing element 20 in that the sensor cell 102 and the pump cell 103 displaced each other in their positions. Namely, the pump cell 103 is located between the reference gas chamber 202 and the sample gas chamber 201. The sensor cell 102 has one electrode located in the sample gas chamber 201 and the other electrode located in the outside of the gas sensing element 40.

Miscellaneous Modifications

The measuring electrode 121 may be made of a material having no chemical activity against NOx gas. For example, the measuring electrode 121 is made of a Au—Pt containing material which is used to form the pump electrodes 131 and 132.

Figure 21:
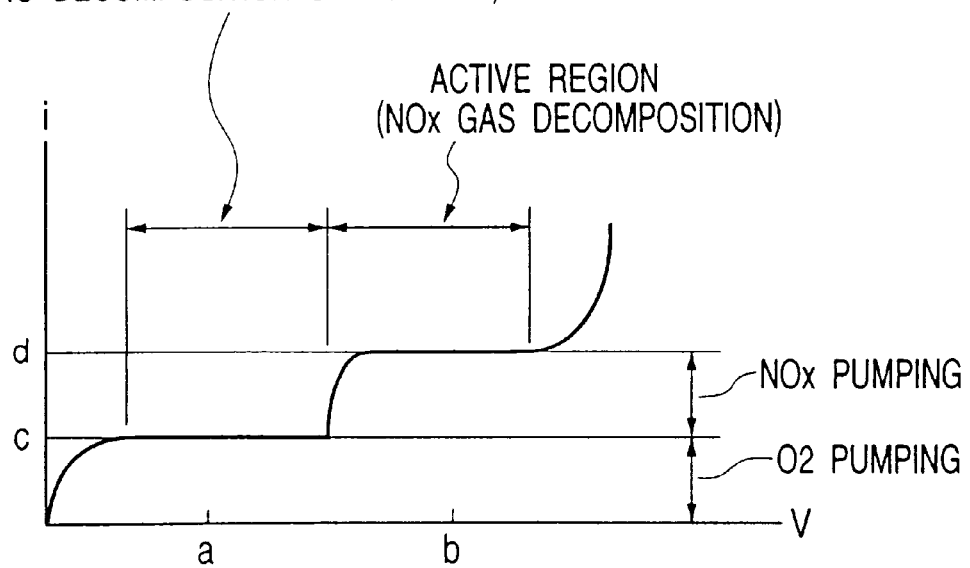
FIG. 21 is a graph showing a voltage-current characteristic curve of a sensor cell in accordance with a modified embodiment of the present invention.

FIG. 21 shows a voltage-current characteristic curve of a Au—Pt electrode in the measurement of a $N_2$—$O_2$—NOx gas. As apparent from FIG. 21, no decomposition of NOx gas occurs when a relatively small voltage is applied to the sensor cell 102. The sensor output derives from only the oxygen pumping operation. A current level "c" represents the limit current. When an increased voltage is applied to the sensor cell 102, the Au—Pt electrode functions as a means for decomposing NOx gas. Thus, another oxygen pumping operation due to the decomposition of the NOx gas is added. In this case, the limit current increases to a current level "d."

Accordingly, when the pump electrode 132 and the measuring electrode 121 are made of the Au—Pt material, the gas sensing element is capable of measuring both the oxygen gas concentration and the NOx gas concentration by selectively setting the voltage level of the sensor cell 102 to "a" and "b."

In the voltage-current characteristic curve shown in FIG. 21, the limit current "c" corresponding to the voltage "a" represents an oxygen gas amount in the vicinity of the sensor cell 102. Thus, this limit current value is used to estimate an offset current corresponding to the residual oxygen. It is possible to cancel such offset current by adequately adjusting circuit component values.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A gas sensing element comprising:
   a sample gas chamber into which a sample gas is introduced;
   a reference gas chamber into which a reference gas is introduced;
   a sensor cell having a measuring electrode located in said sample gas chamber and a reference electrode located in said reference gas chamber for detecting the concentration of a specific gas contained in said sample gas;
   an oxygen pump cell having an inside pump electrode located in said sample gas chamber and an outside pump electrode located on an outside surface thereof for pumping oxygen gas from said sample gas chamber to an outside; and
   an introducing passage including at least one pinhole extending across said oxygen pump cell for introducing said sample gas from the outside into said sample gas chamber,
   wherein
   a porous diffusion resistive layer is provided on said outside surface of said oxygen pump cell so as to cover a portion corresponding to said introducing passage and to help reduce the effect of temperature dependency upon gas element output for a properly sized and placed pinhole.

2. The gas sensing element in accordance with claim 1, wherein a relationship A/B≦0.5 is established when "A" represents a distance from a central position of said introducing passage to a front edge of said outside pump electrode and "B" represents the length of said outside pump electrode.

3. The gas sensing element in accordance with claim 1, wherein said introducing passage has a total cross-sectional area in a range from 0.02 to 0.8 mm .

4. The gas sensing element in accordance with claim 1, wherein
   said sample gas chamber faces both of a first solid electrolytic member and a second solid electrolytic member,
   said reference gas chamber faces said second solid electrolytic member, and
   said oxygen pump cell is provided on said first solid electrolytic member and said sensor cell is provided on said second solid electrolytic member.

5. The gas sensing element in accordance with claim 4, wherein a relationship A/B≦0.5 is established when "A" represents a distance from a central position of said introducing passage to a front edge of an outside pump electrode and "B" represents a length of said outside pump electrode.

6. The gas sensing element in accordance with claim 4, wherein said introducing passage has a total cross-sectional area in a range from 0.02 to 0.8 $mm^2$.

7. A gas sensing element comprising:
   a sample gas chamber into which a sample gas is introduced;
   a reference gas chamber into which a reference gas is introduced;
   a sensor cell located in both of said sample gas chamber and said reference gas chamber for detecting the concentration of a specific gas contained in said sample gas;
   an oxygen pump cell located in said sample gas chamber for pumping oxygen gas from or to said sample gas chamber; and
   an introducing passage including at least one pinhole provided on a surface of said oxygen pump cell for introducing said sample gas into said sample gas chamber,
   wherein said surface of said oxygen pump cell faces an outside of said gas sensing element,
   a porous diffusion resistive layer is provided on said surface of said oxygen pump cell so as to cover a portion corresponding to said introducing passage, and
   said porous diffusion resistive layer has a thickness in a range from 0.05 to 0.3 mm.

8. A gas sensing element comprising:
   a sample gas chamber into which a sample gas is introduced;
   a reference gas chamber into which a reference gas is introduced;
   a sensor cell located in both of said sample gas chamber and said reference gas chamber for detecting the concentration of a specific gas contained in said sample gas;
   an oxygen pump cell located in said sample gas chamber for pumping oxygen gas from or to said sample gas chamber; and
   an introducing passage including at least one pinhole provided on a surface of said oxygen pump cell for introducing said sample gas into said sample gas chamber, wherein said surface of said oxygen pump cell faces an outside of said gas sensing element, a porous diffusion resistive layer is provided on said surface of said oxygen pump cell so as to cover a portion corresponding to said introducing passage, and said porous diffusion resistive layer has a mean pore diameter in a range from 200 to 2,000 Å.

9. A gas sensing element comprising:

a sample gas chamber into which a sample gas is introduced;

a reference gas chamber into which a reference gas is introduced;

a sensor cell located in both of said sample gas chamber and said reference gas chamber for detecting the concentration of a specific gas contained in said sample gas;

an oxygen pump cell located in said sample gas chamber for pumping oxygen gas from or to said sample gas chamber; and an introducing passage including at least one pinhole provided on a surface of said oxygen pump cell for introducing said sample gas into said sample gas chamber, wherein said surface of said oxygen pump cell faces an outside of said gas sensing element, a porous diffusion resistive layer is provided on said surface of said oxygen pump cell so as to cover a portion corresponding to said introducing passage, and said porous diffusion resistive layer has a porosity in a range from 3 to 20%.

10. The gas sensing element in accordance with claim 9, wherein said oxygen pump cell comprises an outside pump electrode provided on an outer surface thereof, and a relationship $A/B \leq 0.5$ is established when "A" represents a distance from a central position of said introducing passage to a front edge of said outside pump electrode and "B" represents a length of said outside pump electrode.

11. The gas sensing element in accordance with claim 9, wherein said introducing passage has a total cross-sectional area in a range from 0.02 to 0.8 mm$^2$.

12. A gas sensing element comprising:

a sample gas chamber into which a sample gas is introduced;

a reference gas chamber into which a reference gas is introduced;

a sensor cell located in both of said sample gas chamber and said reference gas chamber for detecting the concentration of a specific gas contained in said sample gas;

an oxygen pump cell located in said sample gas chamber for pumping oxygen gas from or to said sample gas chamber; and an introducing passage including at least one pinhole provided on a surface of said oxygen pump cell for introducing said sample gas into said sample gas chamber, wherein said surface of said oxygen pump cell faces an outside of said gas sensing element, a porous diffusion resistive layer is provided on said surface of said oxygen pump cell so as to cover a portion corresponding to said introducing passage, and a relationship $0.5 \leq D2/(D1+D2) \leq 0.9$ is established when D1 represents a diffusion resistance of said introducing passage and D2 represents a diffusion resistance of said porous diffusion resistive layer.

13. A method for measuring a specific gas concentration of a sample gas by using a gas sensing element, said gas sensing element comprising:

a sensor cell including a measuring electrode and a reference electrode provided on a solid electrolytic member, said measuring electrode being located in a sample gas chamber and said reference electrode being located in a reference gas chamber;

a pump cell including a pair of pump electrodes provided on opposite surfaces of a solid electrolytic member, one of said pump electrodes being located in said sample gas chamber, wherein said sample gas chamber is filled with a porous member that has a porosity in a range from 3–30%;

a sensor circuit including a first ammeter and a power supplier for measuring a current flowing in said sensor cell; and a pump circuit including a second ammeter and a variable power supplier for measuring a current flowing in said pump cell, and said method comprising:

measuring an oxygen gas concentration of a sample gas based on a current value measured by said second ammeter;

controlling said variable power supplier based on a measured oxygen gas concentration value; and measuring a specific gas concentration of said sample gas based on a current value measured by said first ammeter.

* * * * *